(12) United States Patent
Tseng et al.

(10) Patent No.: US 11,395,745 B2
(45) Date of Patent: *Jul. 26, 2022

(54) SPINAL IMPLANT STRUCTURE AND KIT THEREOF

(71) Applicant: WILTROM CO., LTD., Zhubei (TW)

(72) Inventors: Chang-Ho Tseng, Taipei (TW); Meng-Yuan Tsai, Taipei (TW)

(73) Assignee: WILTROM CO., LTD., Zhubei (TW)

( * ) Notice: Subject to any disclaimer, the term of this patent is extended or adjusted under 35 U.S.C. 154(b) by 190 days.

This patent is subject to a terminal disclaimer.

(21) Appl. No.: 16/737,152

(22) Filed: Jan. 8, 2020

(65) Prior Publication Data

US 2020/0138590 A1 May 7, 2020

Related U.S. Application Data

(62) Division of application No. 15/457,020, filed on Mar. 13, 2017, now Pat. No. 10,555,820.

(30) Foreign Application Priority Data

Mar. 14, 2016 (TW) .................................. 105107739

(51) Int. Cl.
*A61F 2/44* (2006.01)
*A61B 17/88* (2006.01)
*A61F 2/30* (2006.01)

(52) U.S. Cl.
CPC .......... *A61F 2/446* (2013.01); *A61B 17/8852* (2013.01); *A61B 17/8858* (2013.01); *A61F 2002/30593* (2013.01)

(58) Field of Classification Search
CPC .......... A61F 2/44; A61F 2/4455; A61F 2/446; A61F 2002/4475; A61F 2002/4495
See application file for complete search history.

(56) References Cited

U.S. PATENT DOCUMENTS 5,554,191 A * 9/1996 Lahille ............... A61B 17/1757
623/17.11
6,129,763 A * 10/2000 Chauvin ............. A61F 2/30744
623/17.11

(Continued)

FOREIGN PATENT DOCUMENTS

| CN | 102413777 A | 4/2012 |
| CN | 105011993 A | 11/2015 |
| WO | WO-2005/096975 A2 | 10/2005 |

OTHER PUBLICATIONS

European Search Report dated Aug. 16, 2017 in European Patent Application No. 17 16 0573.

(Continued)

*Primary Examiner* — Eric S Gibson
(74) *Attorney, Agent, or Firm* — Muncy, Geissler, Olds & Lowe, P.C.

(57) ABSTRACT

The present invention provides a spinal implant structure. The spinal implant structure comprises a first tube, a second tube and at least one expansion arm. The second tube is disposed on the horizontal orientation of the first tube and does not overlap with the first tube. The diameter of the first tube is larger than that of the second tube. One end of the expansion arm is connected to the first tube, and the other end of the expansion arm is free end. The expansion arm and the first tube create an angle. The expansion arm includes a supporting arm. One end of the supporting arm is connected to the expansion arm, and the other end of the supporting arm is connected the second tube. The support arm, in response to a change in a distance between the first tube and the second tube, drives the expansion arm to move, thereby increasing the included angle and expanding the spinal implant structure.

13 Claims, 48 Drawing Sheets

(56) References Cited

U.S. PATENT DOCUMENTS

| | | | | |
|---|---|---|---|---|
| 6,443,989 B1* | 9/2002 | Jackson | A61F 2/447 | |
| | | | 623/17.15 | |
| 6,652,584 B2* | 11/2003 | Michelson | A61F 2/4455 | |
| | | | 623/17.11 | |
| 6,773,460 B2* | 8/2004 | Jackson | A61F 2/4455 | |
| | | | 623/17.15 | |
| 6,955,691 B2* | 10/2005 | Chae | A61F 2/446 | |
| | | | 623/17.16 | |
| 7,128,760 B2* | 10/2006 | Michelson | A61F 2/446 | |
| | | | 623/17.15 | |
| 7,410,501 B2* | 8/2008 | Michelson | A61F 2/4611 | |
| | | | 623/17.15 | |
| 7,445,636 B2* | 11/2008 | Michelson | A61F 2/446 | |
| | | | 623/17.15 | |
| 7,655,046 B2* | 2/2010 | Dryer | A61F 2/4611 | |
| | | | 623/17.15 | |
| 7,678,148 B2* | 3/2010 | Peterman | A61F 2/4455 | |
| | | | 623/17.11 | |
| 7,879,098 B1 | 2/2011 | Simmons, Jr. | A61F 2/4465 | |
| | | | 623/17.11 | |
| 8,685,095 B2* | 4/2014 | Miller | A61F 2/447 | |
| | | | 623/17.11 | |
| 9,801,733 B2* | 10/2017 | Wolters | A61F 2/447 | |
| 9,814,602 B2* | 11/2017 | Faulhaber | A61F 2/4611 | |
| 9,907,671 B2* | 3/2018 | Fessler | A61F 2/447 | |
| 10,039,650 B2* | 8/2018 | Lamborne | A61F 2/4455 | |
| 10,555,820 B2* | 2/2020 | Tseng | A61B 17/8858 | |
| 2002/0068939 A1 | 6/2002 | Levy et al. | | |
| 2002/0143401 A1* | 10/2002 | Michelson | A61F 2/4611 | |
| | | | 623/17.16 | |
| 2003/0220650 A1 | 11/2003 | Major et al. | | |
| 2005/0021041 A1* | 1/2005 | Michelson | A61F 2/4611 | |
| | | | 606/90 | |
| 2005/0278036 A1* | 12/2005 | Leonard | A61B 17/8858 | |
| | | | 623/23.47 | |
| 2008/0177259 A1 | 7/2008 | Wu | | |
| 2009/0163918 A1 | 6/2009 | Levy et al. | | |
| 2009/0281628 A1* | 11/2009 | Oglaza | A61B 17/7065 | |
| | | | 623/17.15 | |
| 2010/0185291 A1* | 7/2010 | Jimenez | F16C 11/12 | |
| | | | 623/17.16 | |
| 2012/0226357 A1* | 9/2012 | Varela | A61F 2/447 | |
| | | | 623/17.16 | |
| 2015/0012098 A1* | 1/2015 | Eastlack | A61F 2/447 | |
| | | | 623/17.15 | |
| 2016/0135960 A1* | 5/2016 | Grotz | A61F 2/4425 | |
| | | | 623/17.16 | |
| 2017/0095349 A1* | 4/2017 | Asfora | A61F 2/4455 | |
| 2017/0258600 A1* | 9/2017 | Tseng | A61B 17/8852 | |
| 2020/0138590 A1* | 5/2020 | Tseng | A61F 2/446 | |

OTHER PUBLICATIONS

Office Action dated Jul. 23, 2019 in European Applicaiton No. 17 160 573.

\* cited by examiner

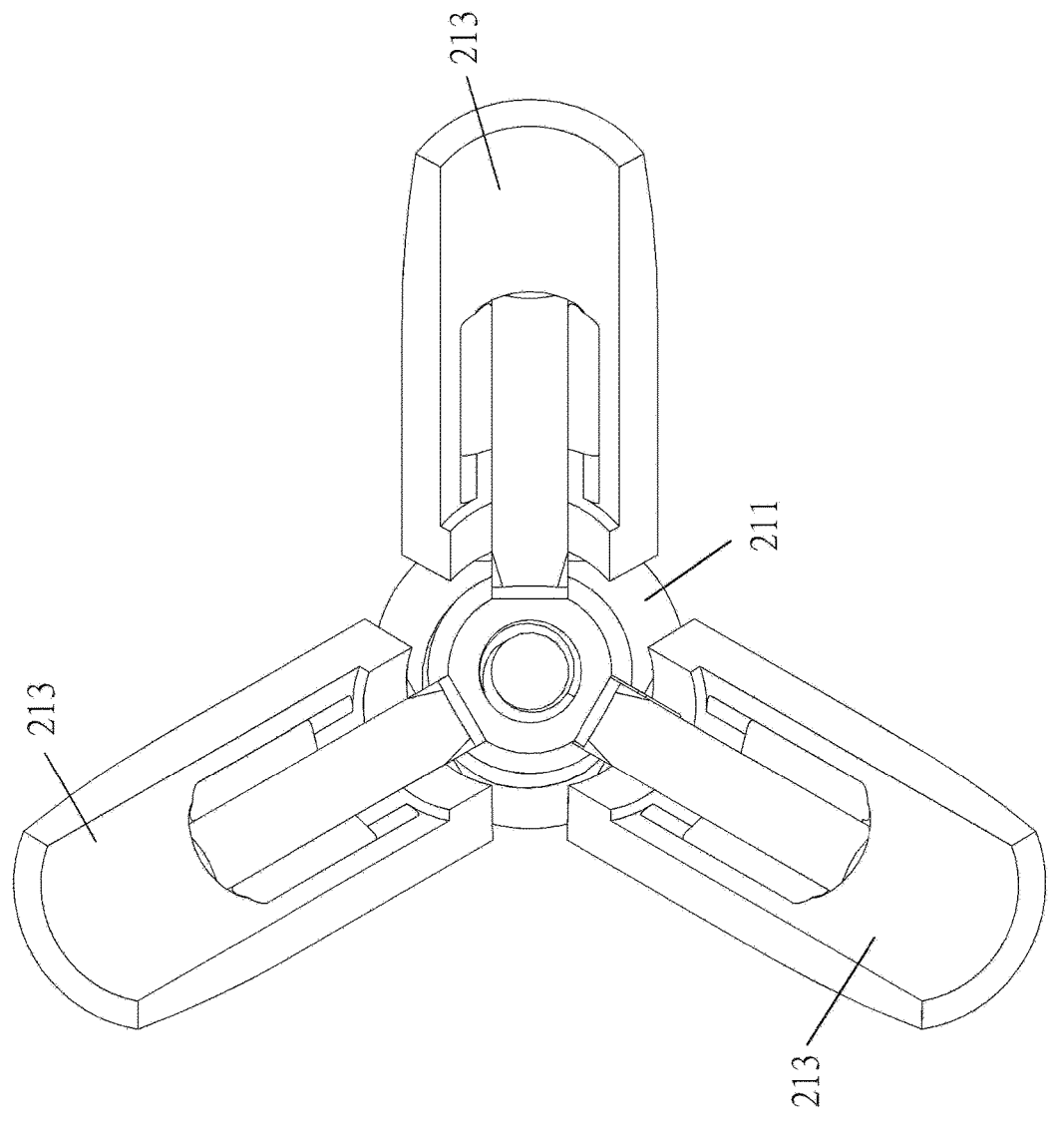

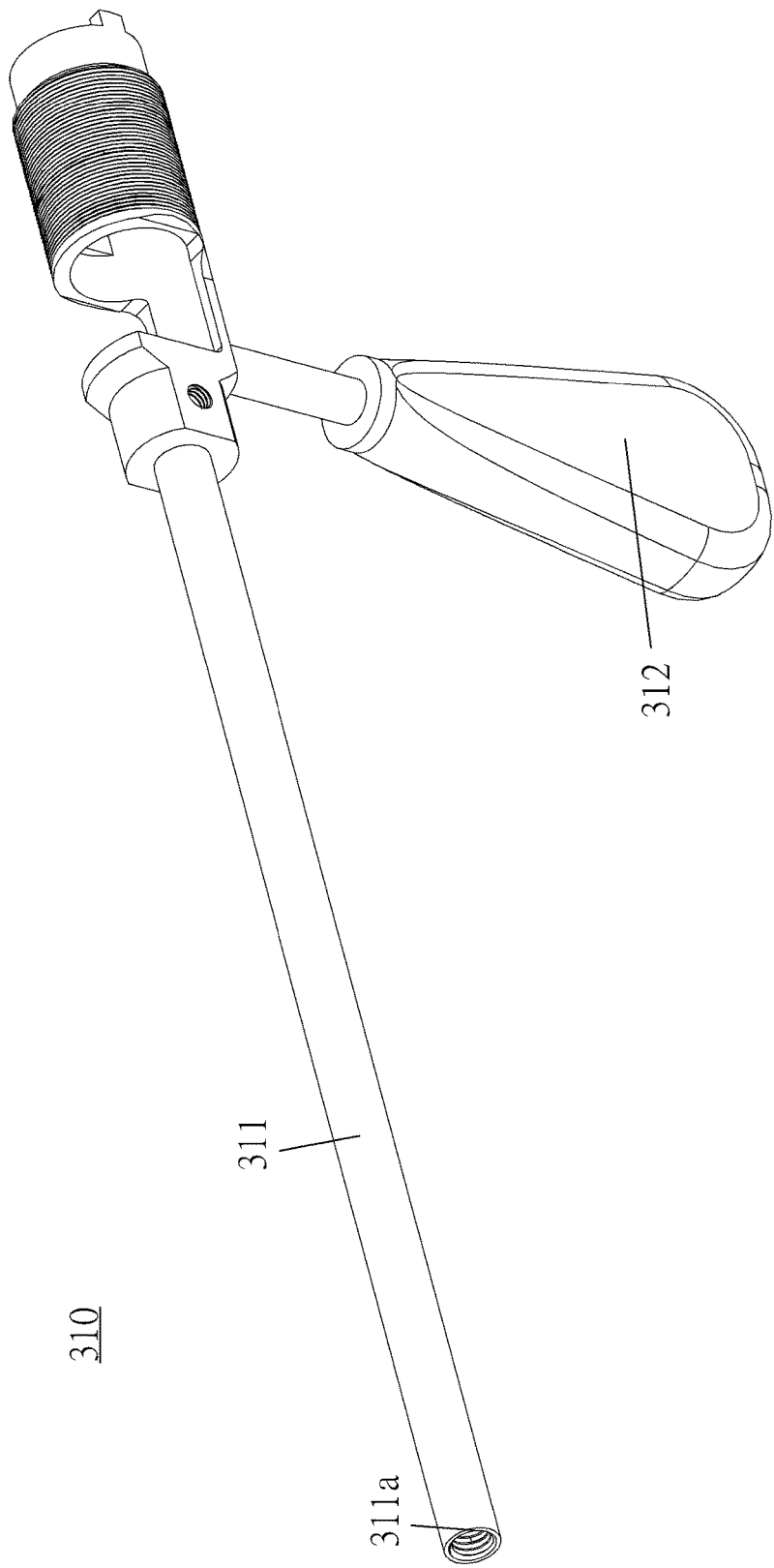

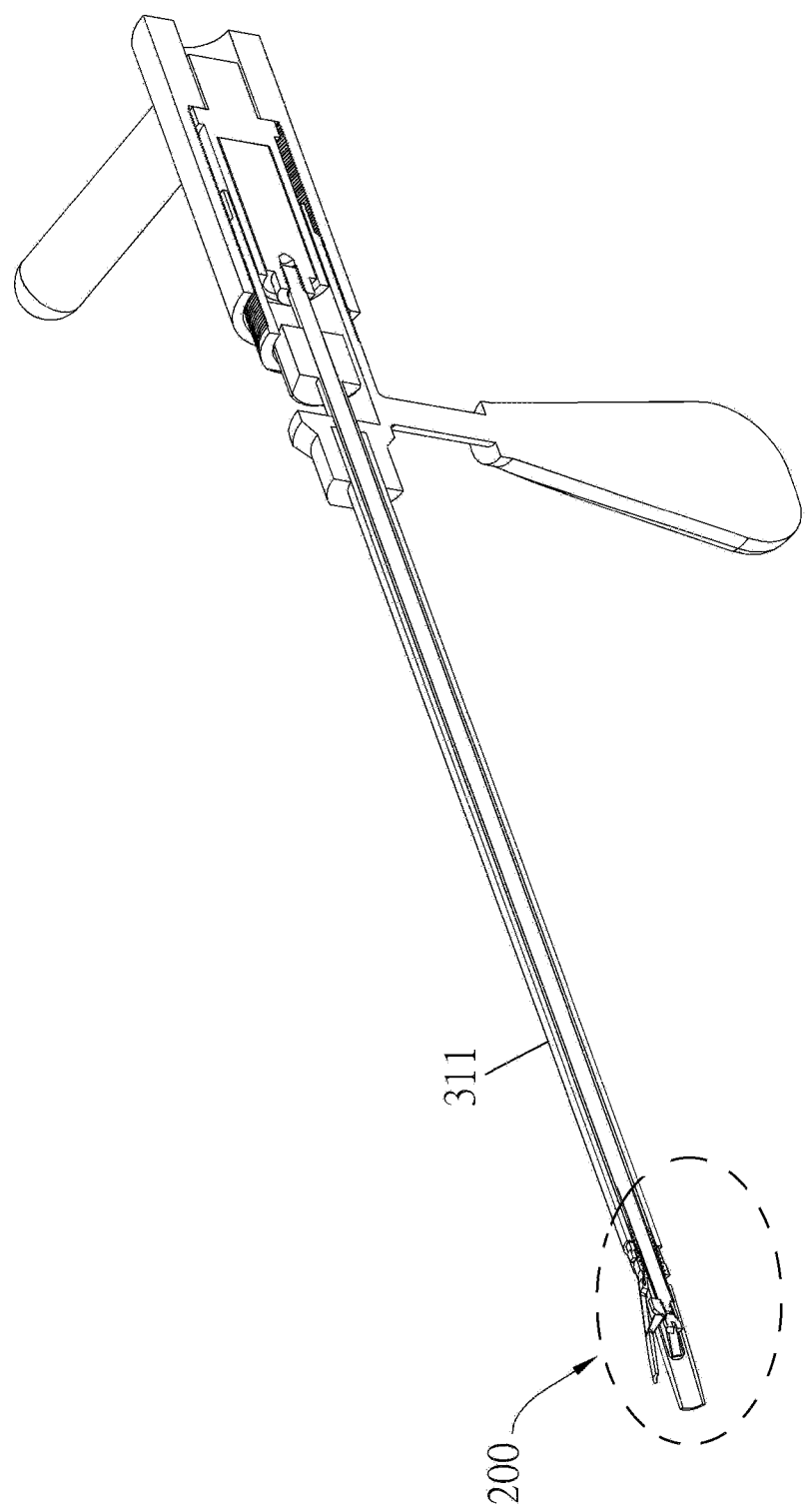

SPINAL IMPLANT STRUCTURE AND KIT THEREOF

CROSS-REFERENCE TO RELATED APPLICATION

This application is a divisional application of U.S. patent application Ser. No. 15/457,020, filed Mar. 13, 2017, which claims priority under 35 U.S.C. § 119(a) to Patent Application No. 105107739 filed in Taiwan on Mar. 14, 2016, all of which are hereby expressly incorporated by reference into the present application.

BACKGROUND OF THE INVENTION

Field of the Invention

The present invention relates to spinal implant structures and, more particularly, to an intervertebral and intravertebral implant and a tool kit thereof.

Description of the Prior Art

The spine, also known as the vertebral column, essentially comprises four types of elements, namely the spinal cord, vertebrae, ligaments, and intervertebral discs. Severe osteoporosis, intervertebral disc degeneration, ligament degeneration, joint dislocation, and joint compression may bring mechanical damage to the spine (such as a spinal compression fracture) and thus destabilize the spine. Spinal instability is accompanied by extreme discomfort and pain, thereby predisposing the patient to chronic back pain, spine curvature disorders, and walking disability.

Among the ways to cure spinal instability is vertebroplasty, which entails placing an implant in a collapsed vertebral body. The implant in the collapsed vertebral body expands and thereby restores the collapsed vertebral body to its normal height. The implant is filled with a bone autograft or a bone substitute (bone cement) to enhance the stability of the spine with a view to curing spinal instability.

A conventional spinal implant structure requires an implanting tool in order to be placed in the collapsed vertebral body and then expands. There is a wide variety of commercially available spinal implant structures and implanting tools. However, the prior art is unsatisfactory and thus still has room for improvement.

SUMMARY OF THE INVENTION

The present invention provides a spinal implant structure kit, comprising a spinal implant structure and an operating tool for use with the spinal implant structure. The spinal implant structure structurally matches the operating tool so that vertebroplasty can be performed efficiently and easily in terms of the adjustment of the position of the spinal implant structure, expansion of the vertebral body, and perfusion of a bone cement, etc.

According to an embodiment of the present invention, a spinal implant structure is provided. The spinal implant structure comprises a first part, a second part, and at least one expansion arm. The second part is disposed along the lengthwise direction of the first part without overlapping the first part. The first part has a larger diameter than the second part. The at least one expansion arm has one end connecting with the first part and forming an included angle with the first part and the other end being a free end. The at least one expansion arm has a support arm. The support arm has one end connecting with the expansion arm and the other end connecting with the second part. The support arm comprises a plurality of weakened regions. In response to a change in the distance between the first part and the second part, the support arm bends at the weakened regions and thus drives the expansion arm to move, so as to increase the included angle and expand the spinal implant structure. The first part, second part, expansion arm, and support arm are formed integrally.

In another embodiment of the present invention, a spinal implant kit comprises the spinal implant structure and the operating tool. The operating tool comprises a tool body, a fixing sleeve, a central rod, and an operating handle. The tool body has a connecting portion and a gripping portion. The connecting portion has a tail provided with a jointing structure for connecting with the spinal implant structure. The fixing sleeve fits inside the tool body to fix the distance between a first part and a second part of the spinal implant structure. The central rod fits inside the fixing sleeve to connect with the second part directly or connect with the second part through the fixing sleeve. The operating handle connects with the central rod and rotates to drive the central rod to move in the lengthwise direction of the first part.

To render the above and other aspects of the present invention comprehensible, the present invention is hereunder illustrated by embodiments and accompanying drawings.

BRIEF DESCRIPTION OF THE DRAWINGS

FIG. 1A through FIG. 4B are schematic views of a spinal implant structure according to an embodiment (first embodiment) of the present invention.
FIG. 1A and
FIG. 1B show that the spinal implant structure is folded (i.e., not netted).
FIG. 4A and FIG. 4B show that the spinal implant structure (i.e., netted) has been expanded.

FIG. 5A through FIG. 8B are schematic views of the spinal implant structure according to another embodiment (second embodiment) of the present invention. FIG. 5A and FIG. 5B show that the spinal implant structure (i.e., not netted) is folded. FIG. 6A through FIG. 6C show that the spinal implant structure (i.e., not netted) has been expanded. FIG. 8A through FIG. 8B show that the spinal implant structure (i.e., netted) has been expanded.

FIG. 9A through FIG. 15A are schematic views of the operating tool, respectively.

FIG. 16A through FIG. 18B are schematic views of the spinal implant structure and the operating tool coupled thereto according to the first embodiment of the present invention.

FIG. 19A through FIG. 20C are schematic views of the spinal implant structure and the operating tool coupled thereto according to the second embodiment of the present invention.

FIGS. 1A, 2A, 3A, 4A, 5A, 6A, 7A, 8A, 9A, 10A, 11A, 12A, 13A, 14A, 15A, 16A, 17A, 18A, 19A, 20A, 21A are lateral views. FIGS. 1B, 2B, 3B, 4B, 5B, 6B, 7B, 8B, 9B, 10B, 11B, 12B, 13B, 14B, 16B, 17B, 18B, 19B, 20B, 21B are cross-sectional views. FIGS. 2C, 6C, 10C, 16C, 17C, 19C, 20C are front views or partial enlarged views.

The aforesaid diagrams, which merely serve exemplary purposes to illustrate the shapes and relative positions of the constituent elements of the present invention, are not drawn to scale.

Due to the limits of drawing software, a mark, for example, indicative of an anchor A or contact, may be shown in the aforesaid diagrams, but the anchor A or contact is optional rather than required.

DETAILED DESCRIPTION OF THE EMBODIMENTS

The present invention provides a spinal implant kit which comprises a spinal implant structure and an operating tool. The spinal implant structure is made of a metal or a biocompatible polymer. The metal includes a titanium alloy, whereas the biocompatible polymer includes polyether-ether-ketone (PEEK) and its derivatives. PEEK and cancellous bone are closely in hardness. Furthermore, carbon fiber reinforced PEEK, which is as hard as cortical bone, is applicable to the spinal implant kit of the present invention. However, the present invention is not restrictive of the materials which the spinal implant kit of the present invention is made of, and thus the spinal implant kit of the present invention may also be made of the other biocompatible materials.

Spinal Implant Structure

FIG. 1A through FIG. 8C illustrate two different embodiments of a spinal implant structure of the present invention. FIG. 1A through FIG. 4B show a spinal implant structure 100 of the first embodiment of the present invention. FIG. 5A through FIG. 8C show a spinal implant structure 200 of the second embodiment of the present invention.

First Embodiment

Figure 1A:
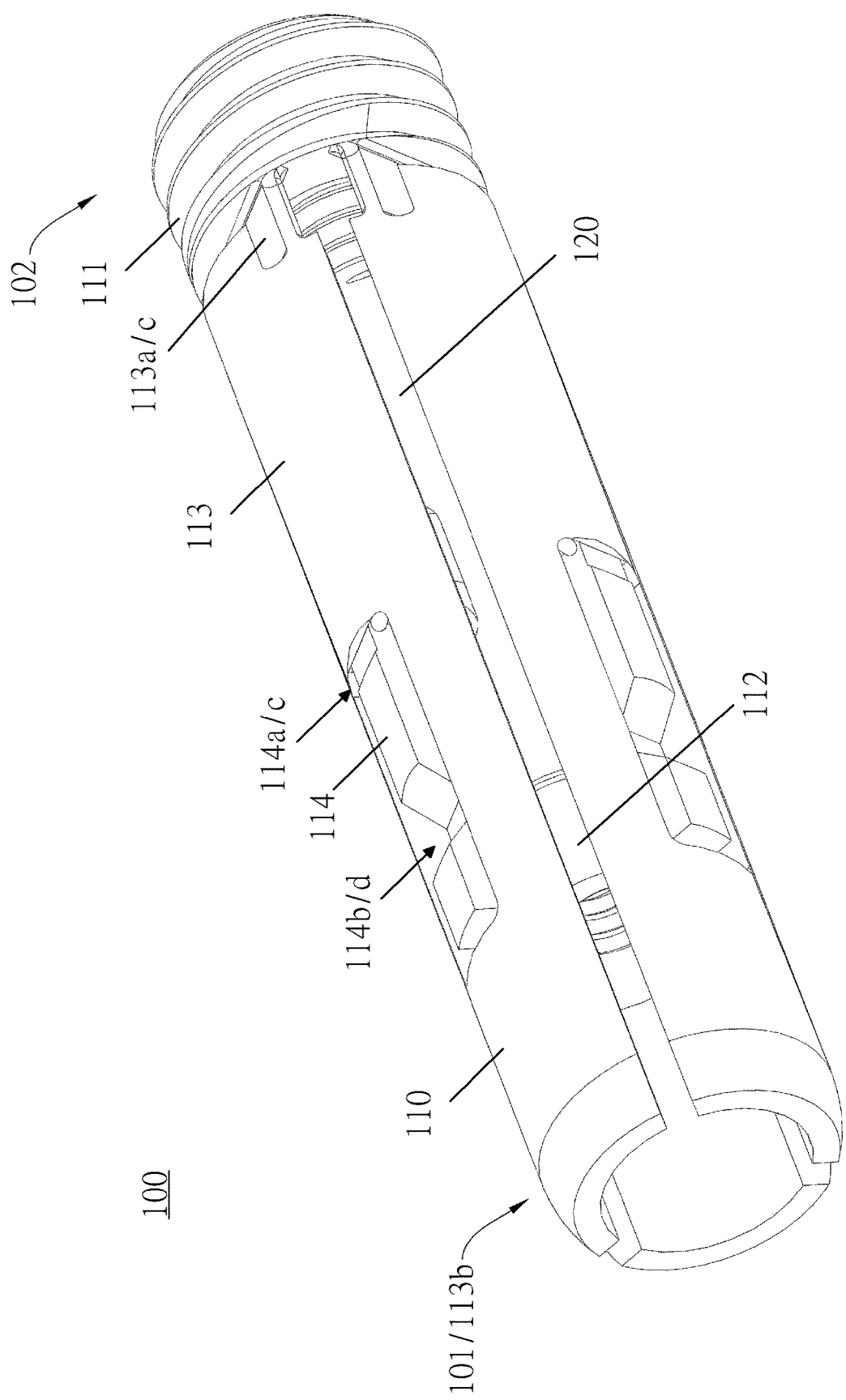
Figure 1B:
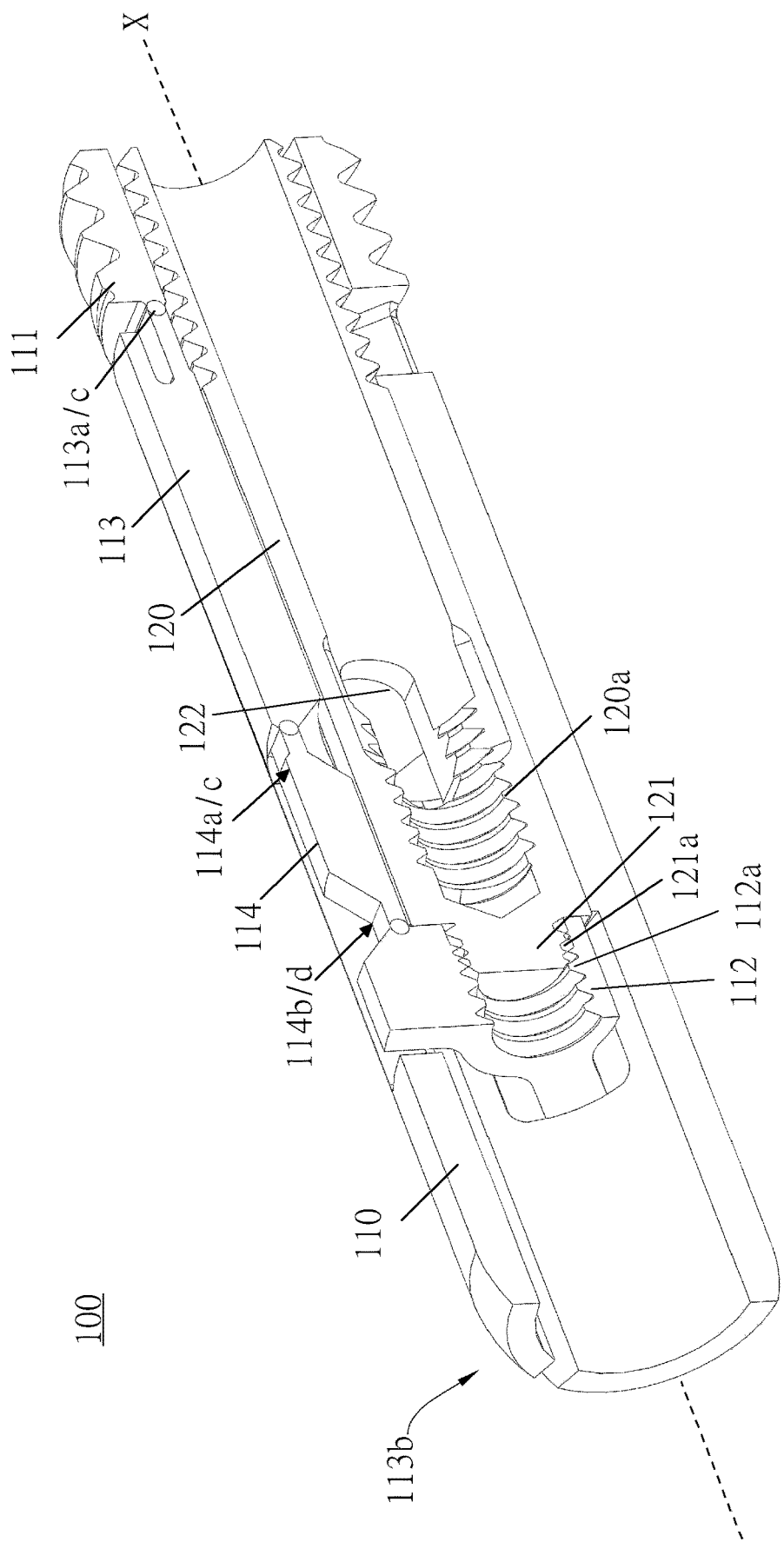
Figure 2A:
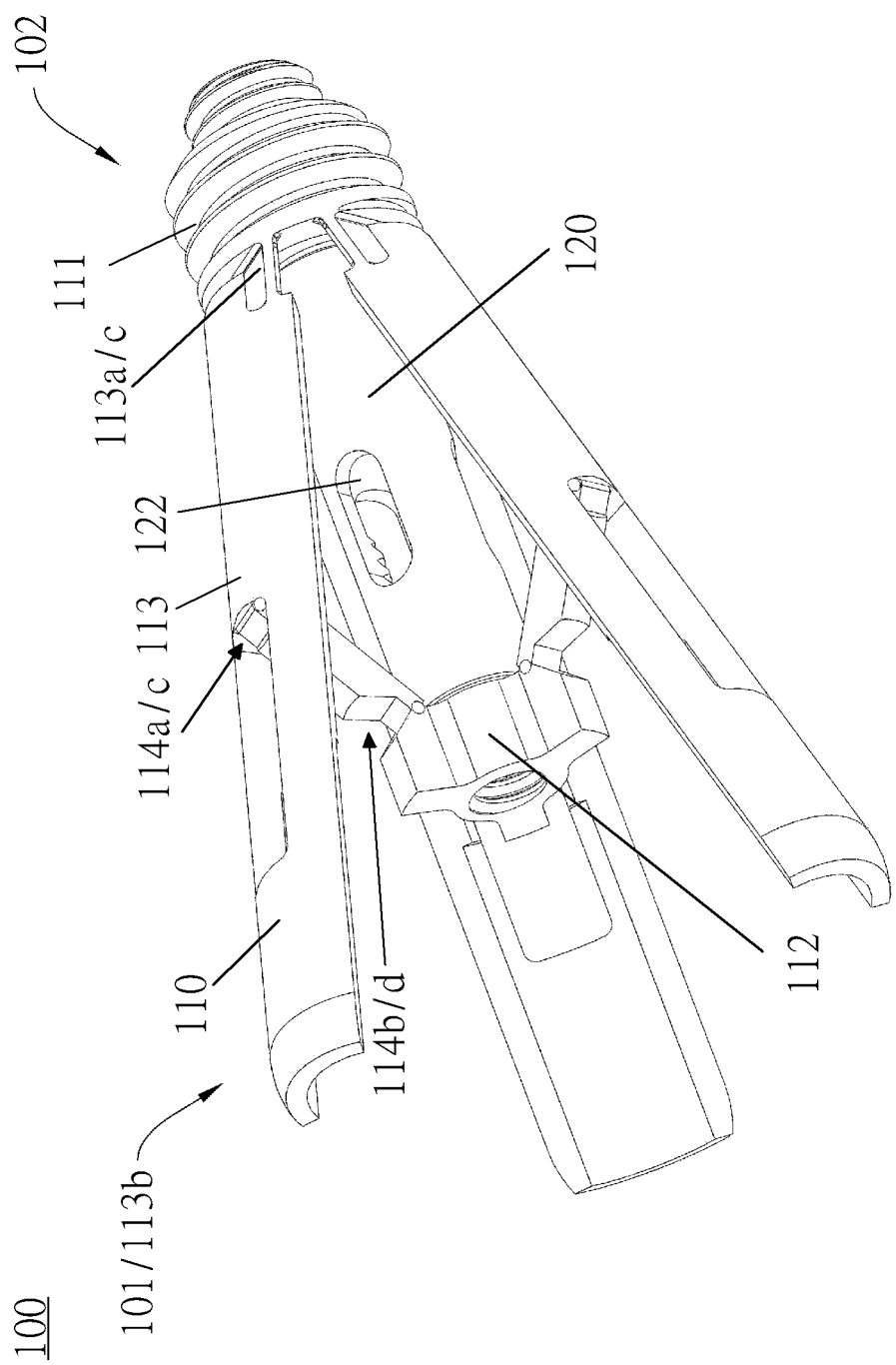
FIG. 2A through FIG. 2C show that the spinal implant structure (i.e., not netted) has been expanded.
Figure 2B:
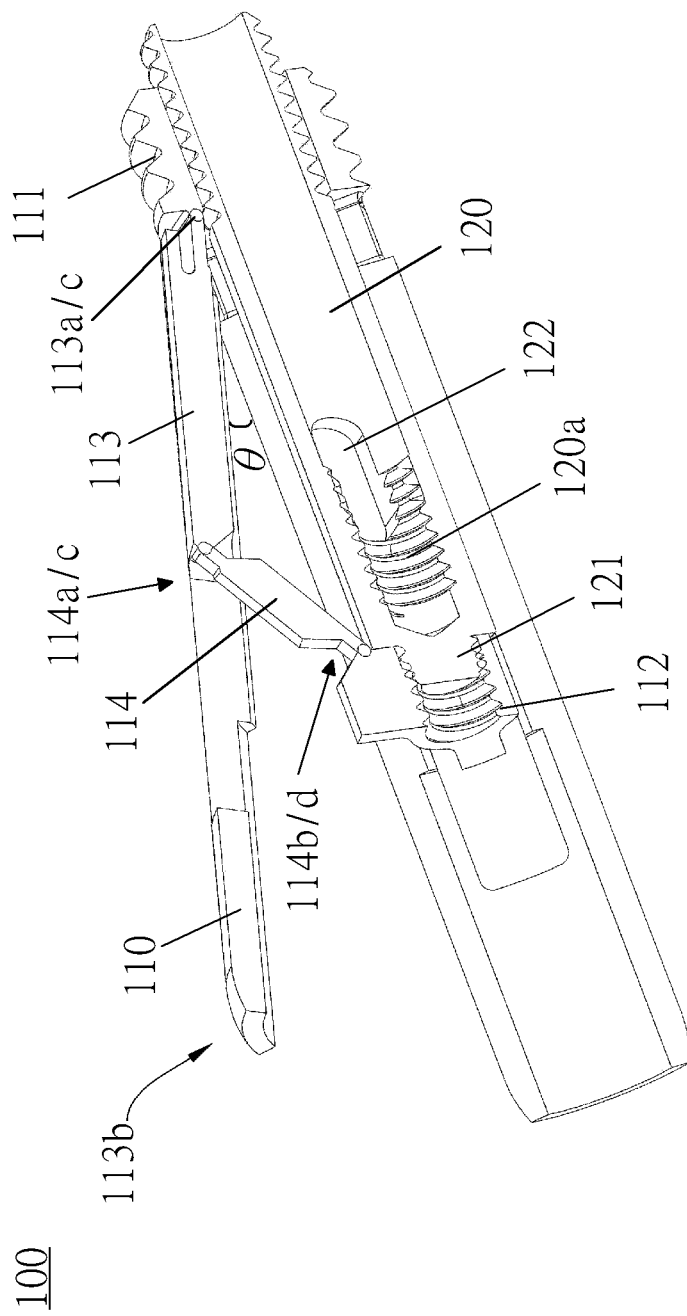
Figure 2C:
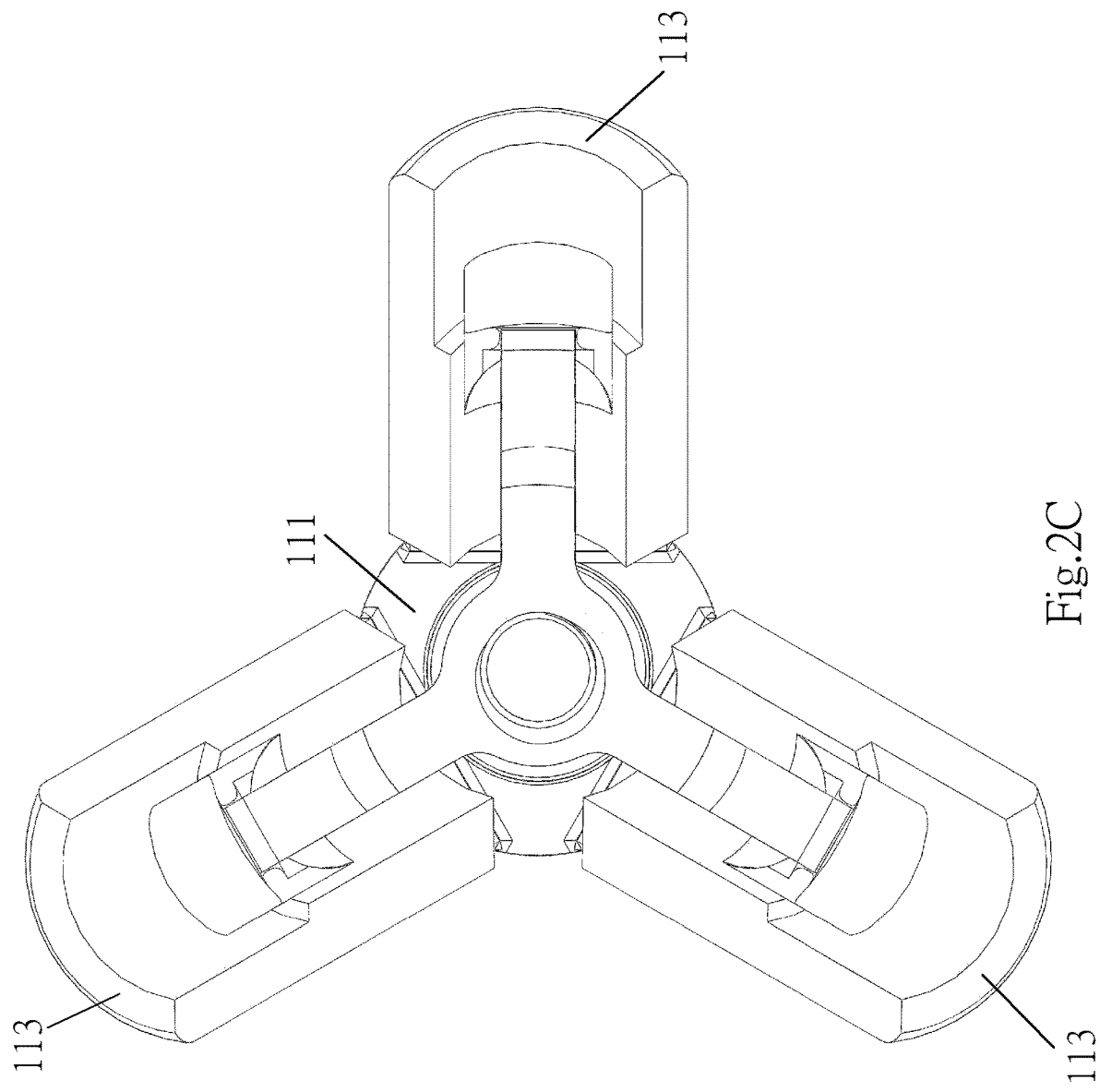

The spinal implant structure 100, which is not netted, is illustrated by FIG. 1A through FIG. 2C. Referring to FIG. 1A and FIG. 1B, there are shown a lateral view and a cross-sectional view of the spinal implant structure 100 which is folded, respectively. FIG. 2A through FIG. 2C are a lateral view, a cross-sectional view, and a front view of the spinal implant structure 100 which has been expanded, respectively. Referring to FIGS. 1A, 1B, 2A, 2B, the spinal implant structure 100 comprises a body 110 and a fixing screw barrel 120. When the spinal implant structure 100 is folded, the body 110 becomes a hollow-cored cylinder, and the fixing screw barrel 120 also becomes a hollow-cored cylinder. The spinal implant structure 100 has an expansion end 101 (left end) and a fixing end 102 (right end). The expansion end 101 is expanded with the operating tool (referring to FIG. 1A and FIG. 2A), and the degree of expansion can be adjusted as needed.

[Body]

The body 110 of the spinal implant structure 100 comprises a first part 111, a second part 112, an expansion arm 113, and a support arm 114, and the four parts are formed integrally. Both the first part 111 and the second part 112 are hollow-cored cylinders. The first part 111 and the second part 112, which are separated and do not overlap (engage), are arranged along the same horizontal axis (X-axis, FIG. 1B). That is, the first part 111 and the second part 112 are two smaller independent tubes (which may also be called the first tube 111 and the second tube 112) split from the body 110, and the two parts are connected by the expansion arm 113 and the support arm 114. The first part 111 contains the fixing screw barrel 120. The second part 112 contains a fixing component and a netting (to be described later.) The first part 111 has an inner diameter slightly larger than the second part 112 and a length slightly longer than the length of the second part 112. The degree of the expansion of the spinal implant structure 100 can be changed by adjusting the distance between the first part 111 and the second part 112. In this embodiment, the degree of the expansion of the spinal implant structure 100 increases, as the first part 111 and the second part 112 get closer to thereby reduce the distance therebetween along the horizontal axis (X-axis). Hence, an operating tool (a central rod, to be described later) is required to draw the second part 112 closer to the first part 111 (i.e., rightward) in order for the spinal implant structure 100 to expand.

The bending of the expansion arm 113 enables the spinal implant structure 100 to expand. An end 113a (first end) of the expansion arm 113 connects with the first part 111 and extends outward from the first part 111. The other end 113b (second end) of the expansion arm 113 is a free end which does not connect with any other component. A stress weakening portion (weakened section) is defined at a junction 113c of the expansion arm 113 and the first part 111. The stress weakening portion is, for example, made thin or hollowed out so that the stress weakening portion (weakened section) is weaker than its surroundings. When subjected to an applied force, the expansion arm 113 bends outward from the stress weakening portion to effectuate expansion. The stress weakening portion is a notch which may have a valley, a concave, a V-, a U-shape, etc. An included angle θ (shown in FIG. 2B) smaller than 90 degrees is formed between the expansion arm 113 and the extension line of the first part 111. The included angle θ indicates the degree of the expansion of the spinal implant structure 100. The included angle θ equals 0 degree when the spinal implant structure 100 is folded (FIG. 1A and FIG. 1B). The included angle θ is larger than 0 degree but smaller than 90 degrees when the spinal implant structure 100 has been expanded (FIG. 2A and FIG. 2B). The expansion arm 113 is in the number of one or more. If the expansion arm 113 is in the number of two or more, the expansion arms 113 connected to the first part 111 are equally spaced apart. As shown in FIG. 2C, in this embodiment, the spinal implant structure 100 comprises three expansion arms 113 spaced apart by 120 degrees. In another embodiment of the present invention, the expansion arms are in the number of two (and thus spaced apart by 180 degrees), four (and thus spaced apart by 90 degrees) or more. The more the expansion arms are provided, the more uniform the distribution of forces required to effectuate expansion is, the smaller each expansion arm is, and the stricter the requirement for product precision is.

The expansion arm 113 (expansion arm body) has therein a support arm 114. The support arm 114 is tongue-like in shape and can be considered as split from the expansion arm 113; in other words, the support arm 114 and the expansion arm 113 are formed integrally. Or, the expansion arm 113 and the support arm 114 can both be considered as split from the body 110. When the support arm 114 and the expansion arm 113 are integrally formed and split from the body 110, the manufacturing process of the spinal implant structure 100 can be further simplified. An end 114a (first end) of the support arm 114 is not only connected to the inner side of the expansion arm 113, but also connected to the expansion arm 113 in a manner to be positioned proximate to the first part 111. The other end 114b (second end) of the support arm 114 is connected to the second part 112 in a manner to be positioned proximate to the first part 111. At least one stress weakening portion (weakened section) is defined at the support arm 114. This embodiment is exemplified by two stress weakening portions located at a junction 114*c* of the support arm 114 and the expansion arm 113 and a junction 114*d* of the support arm 114 and the second part 112, respectively. In response to a reduction in the distance between the first part 111 and the second part 112, the support arm 114 bends at the stress weakening portions under a force. As shown in FIG. 2B, at the stress weakening portion 114*c*, the support arm bends toward the inner side of the spinal implant structure 100, whereas, at the stress weakening portion 114*d*, the support arm 114 bends toward the outer side of the spinal implant structure 100, thereby driving the expansion arm 113 to bend toward the outer side of the spinal implant structure 100 and thus increasing the included angle θ, so as for the spinal implant structure 100 to expand. The stress weakening portions are, for example, made thin or hollowed out so that the stress weakening portions are weaker than their surroundings; hence, when the support arm 114 is subjected to an applied force, the resultant stress is concentrated on the stress weakening portions, thereby causing structural deformation of the support arm 114 (i.e., the bending of the support arm 114). In the expansion process of the spinal implant structure 100, the distance between the first part 111 and the second part 112 decreases until the both parts meet. However, the first part 111 and the second part 112 do not overlap with or engage each other.

The body 110 of the spinal implant structure 100 is preferably formed integrally, for example, by molding, lathing, milling, electrical discharge machining (EDM), 3D printing, or pressing, to form the first part 111, the second part 112, the expansion arm 113, and the support arm 114 by a one-off process.

[Fixing Screw Barrel]

Like the body 110, the fixing screw barrel 120 is a hollow-cored cylinder. The fixing screw barrel 120 fixes the distance between the first part 111 and the second part 112 upon completion of the expansion of the spinal implant structure 100. The fixing screw barrel 120 has a smaller diameter than the first part 111 so as to fit inside the first part 111. The fixing screw barrel 120 has an end positioned proximate to the second part 112, and the end has a protruding portion 121. The diameter of the protruding portion 121 substantially equals the inner diameter of the second part 112. The outer surface of the protruding portion 121 has a first outer thread 121*a*. The first outer thread 121*a* matches a first inner thread 112*a* disposed on the inner surface of the second part 112; hence, the protruding portion 121 can be rotated and inserted into the second part 112 so as to be fixed thereto, allowing the fixing screw barrel 120 to abuttingly connect with the second part 112. A second inner thread 120*a* is disposed on the inner surface of the fixing screw barrel 120. The second inner thread 120*a* matches the outer thread (to be described later) of the central rod of the operating tool. After rotating and inserting the central rod into the fixing screw barrel, the user can pull the central rod and thereby drive the fixing screw barrel 120 and the second part 112 to move, allowing the second part 112 to get closer to the first part 111, so as to effectuate the expansion of the spinal implant structure 100.

Referring to FIG. 1B, when the spinal implant structure 100 is folded, the tail (right end) of the fixing screw barrel 120 is contained in the first part 111. Referring to FIG. 2B, when the spinal implant structure 100 has been expanded, the second part 112 moves toward the first part 111, and the tail of the fixing screw barrel 120 protrudes from the first part 111. Another screw nut (not shown, derived from the operating tool) fits around the protruding part of the tail of the fixing screw barrel 120 to prevent the fixing screw barrel 120 from moving toward the second part 112, thereby fixing the distance between the first part 111 and the second part 112. To fit the fixing screw barrel 120 inside the other screw nut, an outer thread is disposed on a portion of the outer surface (tail) of the fixing screw barrel 120.

The wall of the fixing screw barrel 120 has one or at least two through holes 122 whereby a bone cement enters the vertebral body during the bone cement perfusion step (to be described later).

When the spinal implant structure 100 is in an expansion position (FIG. 2A), it has a larger internal volume than when it is folded (FIG. 1A), and can therefore support and restore a damaged/collapsed vertebral body; also, a large amount of bone cement can be filled in the spinal implant structure 100 to reinforce the support.

[Netting]

Figure 3A:
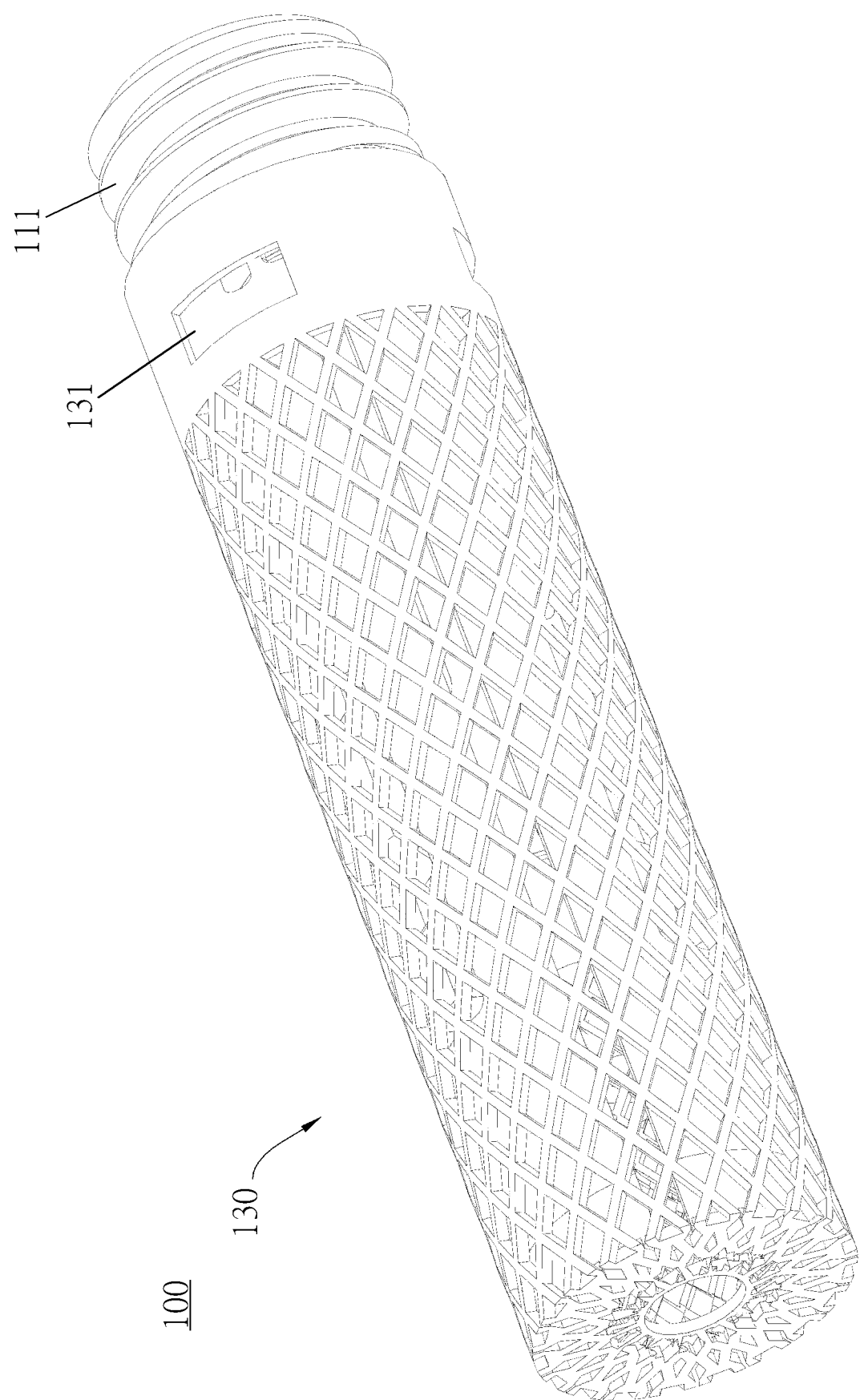
FIG. 3A and FIG. 3B show that the spinal implant structure (i.e., netted) is folded.
Figure 3B:
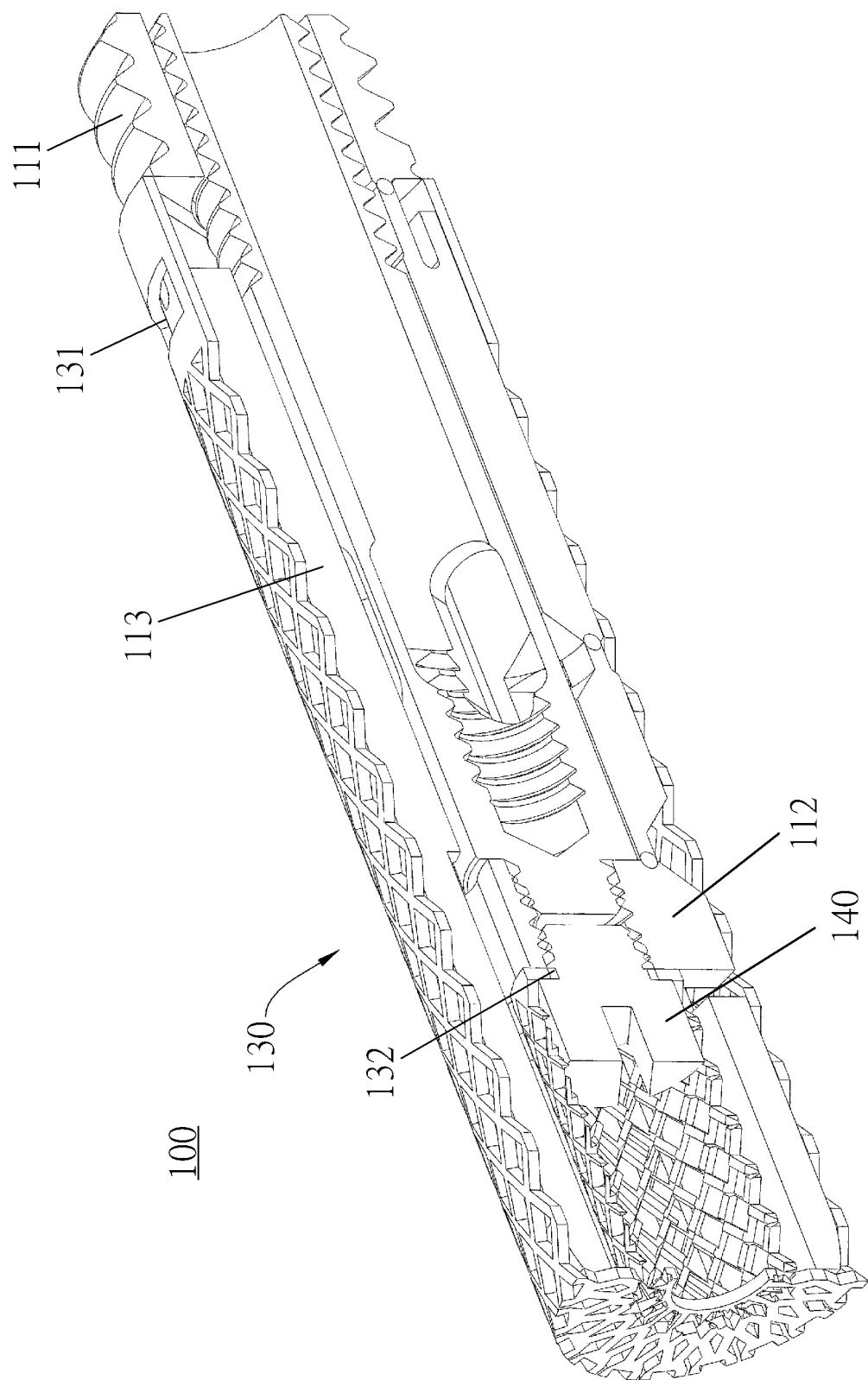
Figure 4A:
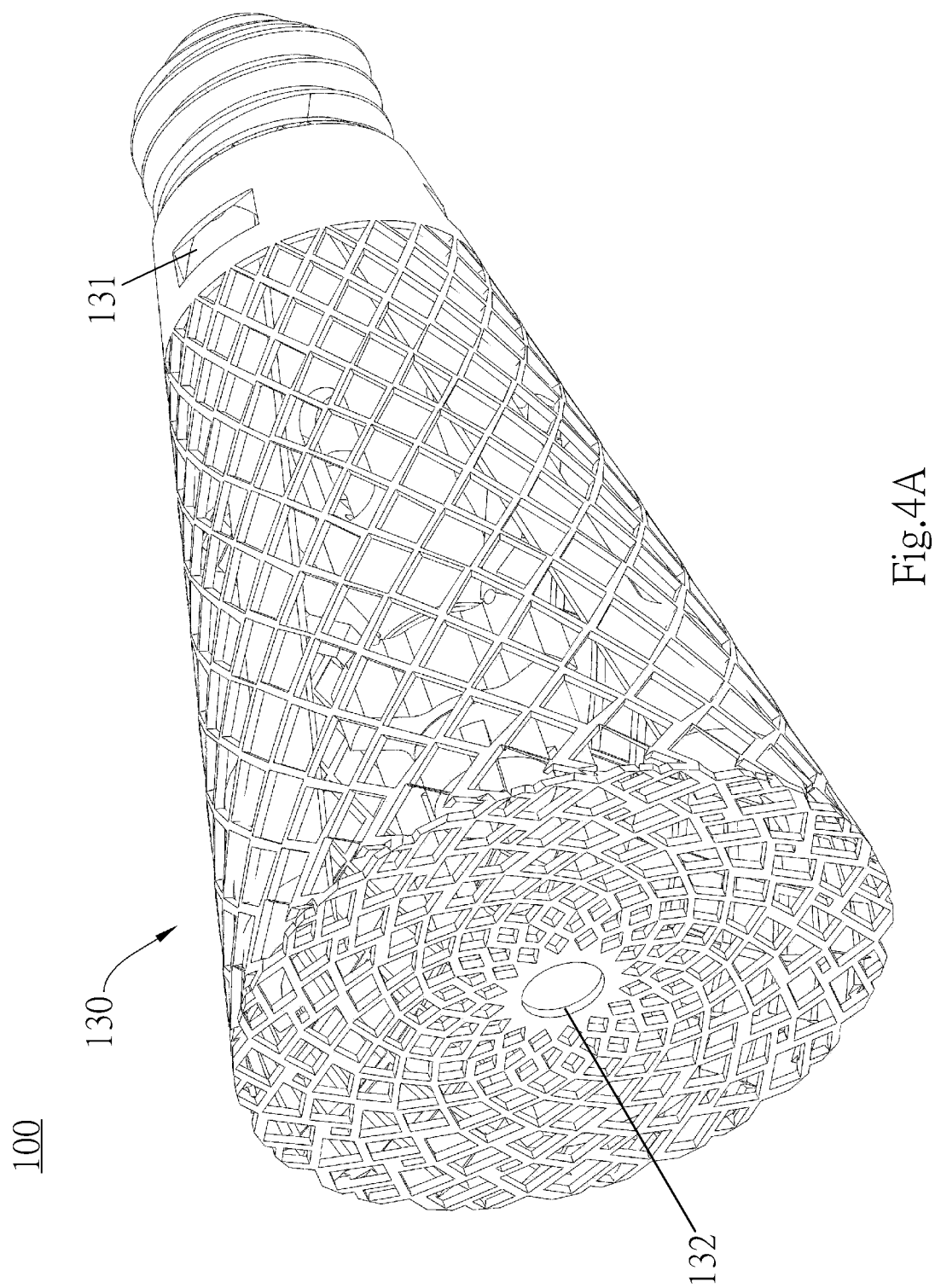
Figure 4B:
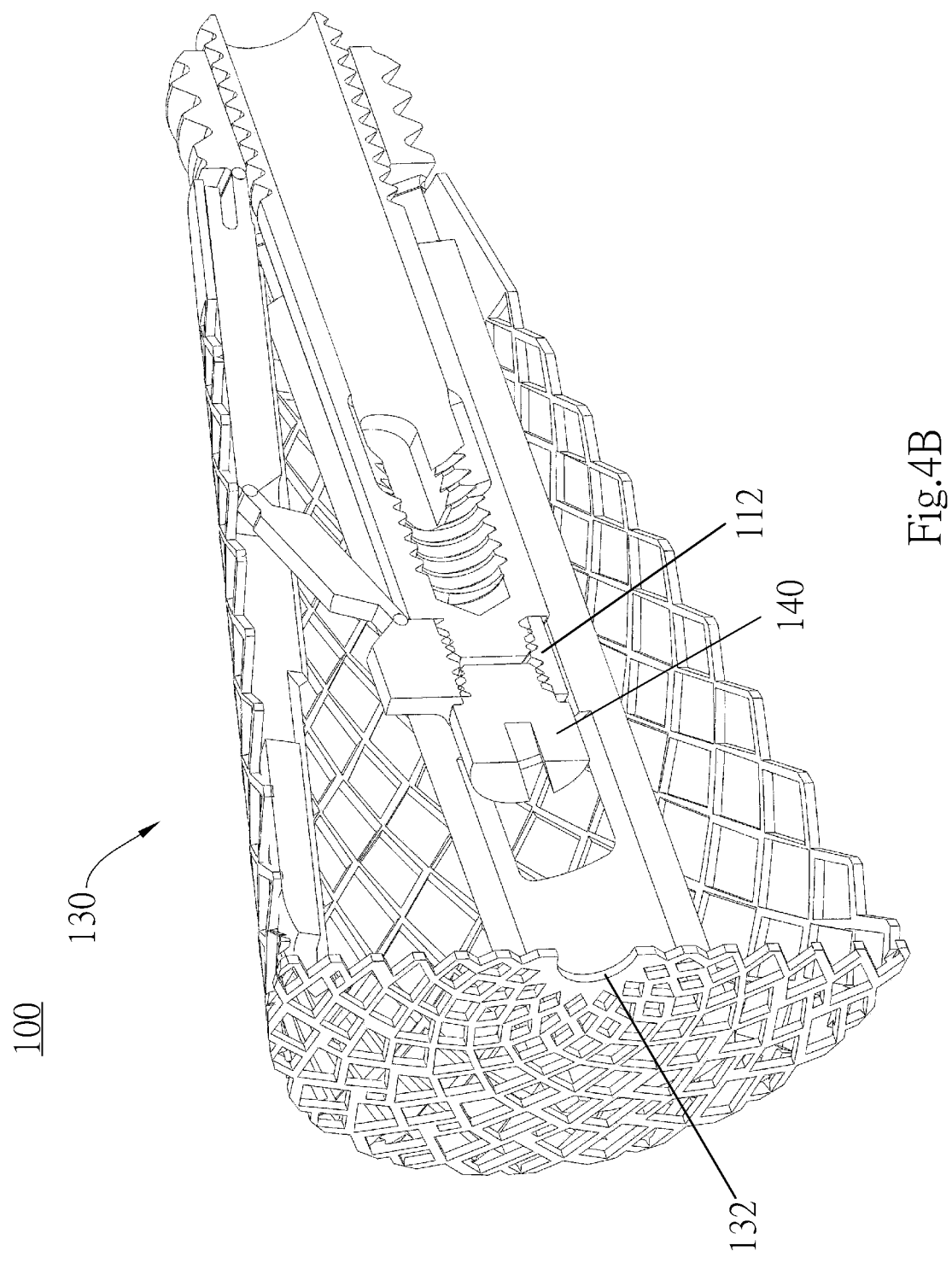

FIG. 3A through FIG. 4B show that the spinal implant structure 100 has a netting 130 mounted thereon. FIG. 3A and FIG. 3B show that the spinal implant structure 100 is folded. FIG. 4A and FIG. 4B show that the spinal implant structure 100 has been expanded. The netting 130 restricts the range of flow of the bone cement being perfused into the spinal implant structure 100, so as to prevent the bone cement from spilling from the vertebral body, allow the spinal implant structure 100 to be uniformly expanded, and reinforce the vertebral body.

The netting 130 is hollow-cored and cylindrical in shape. The netting 130 fits around the expansion arm 113 of the spinal implant structure 100 and can unfold as a result of the expansion of the spinal implant structure 100 (FIG. 4B). The openings at the two ends of the netting 130 differ in size. The sidewall of the end with a larger opening has at least one engaging hole 131. The end is engaged with a first part-facing end of the expansion arm 113. The other end of the netting 130 has a fixing hole 132 of a smaller diameter (FIG. 4A). When the spinal implant structure 100 is folded (FIG. 3B), one end of the netting 130 is fixed to the expansion arm 113 through the engaging hole 131, whereas the other end of the netting 130 is bent to be inserted into the spinal implant structure 100, and in consequence a fixing component 140 is fixed to the second part 112 through the fixing hole 132. The fixing component 140 is, for example, a screw whose thread enables it to be rotated and inserted into the second part 112. The outer diameter of the screw's head is slightly larger than the diameter of the fixing hole 132 of the netting 130. Hence, the netting 130 is fixed in place between the screw's head and thread; in other words, the netting 130 is fixed in place at the junction of the fixing component 140 and the second part 112. In this embodiment, the netting 130 is disconnectably engaged between the fixing component 140 and the second part 112; hence, when the spinal implant structure 100 is expanded (FIGS. 4A, 4B), that is, at the time when the second part 112 moves toward the first part 111 under a pulling force, the netting 130 is disconnected from the fixing component 140 under the pulling force, thereby allowing the netting 130 to unfold as a result of the expansion of the spinal implant structure 100. There are plenty of ways to disconnect the netting 130 from the fixing component 140, including making the screw head of the fixing component 140 slightly larger than the fixing hole 132 and defining it with a lead angle, or providing several notches on the fixing hole 132, but the present invention is not limited thereto. Therefore, when the second part 112 moves toward the first part 111 under a pulling force, the netting 130 can be easily disconnected from the fixing component 140 under a reverse pulling force.

Second Embodiment

FIG. 5A through FIG. 6C show that the spinal implant structure 200 is not netted. The spinal implant structure 200 of the second embodiment is identical to the spinal implant structure 100 of the first embodiment in terms of most technical features. For the sake of brevity, the identical technical features are not described herein.

Figure 5A:
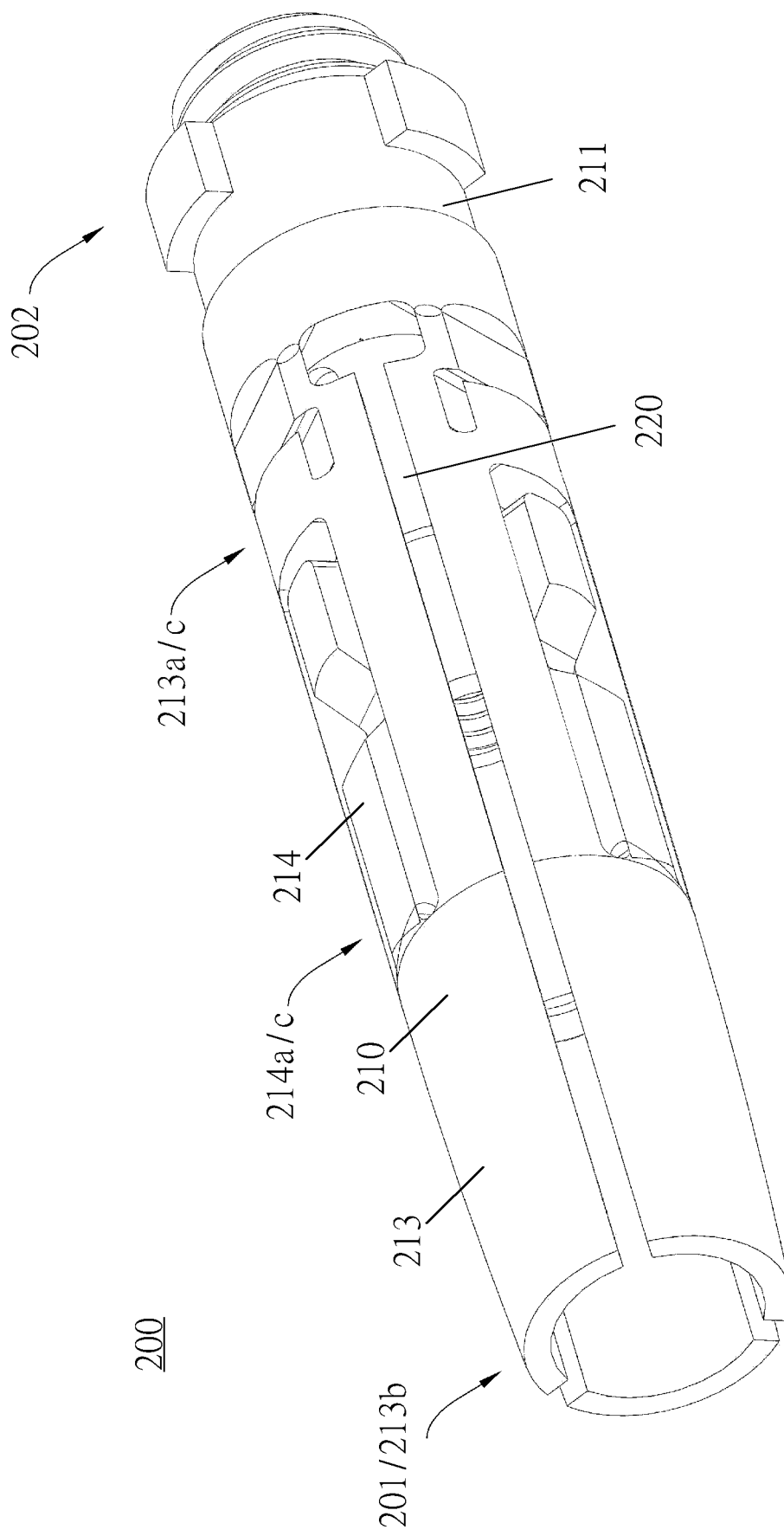
Figure 5B:
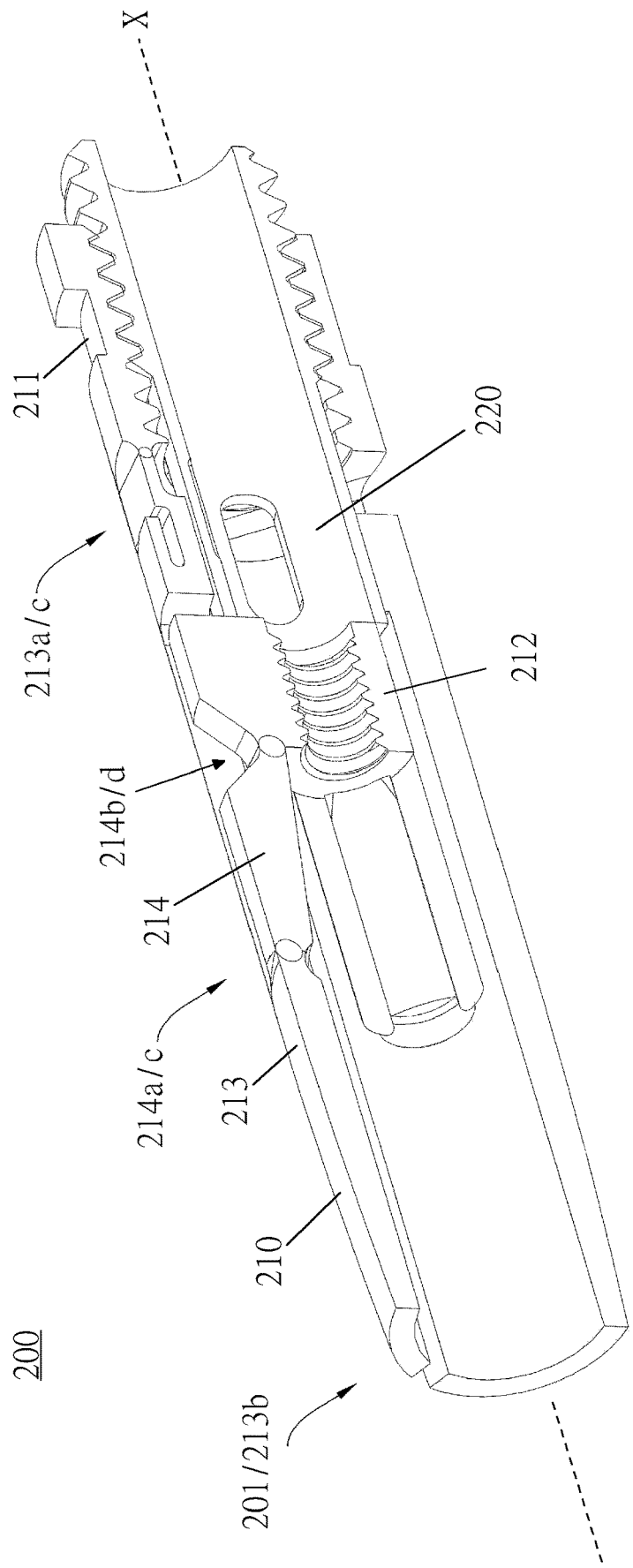
Figure 6A:
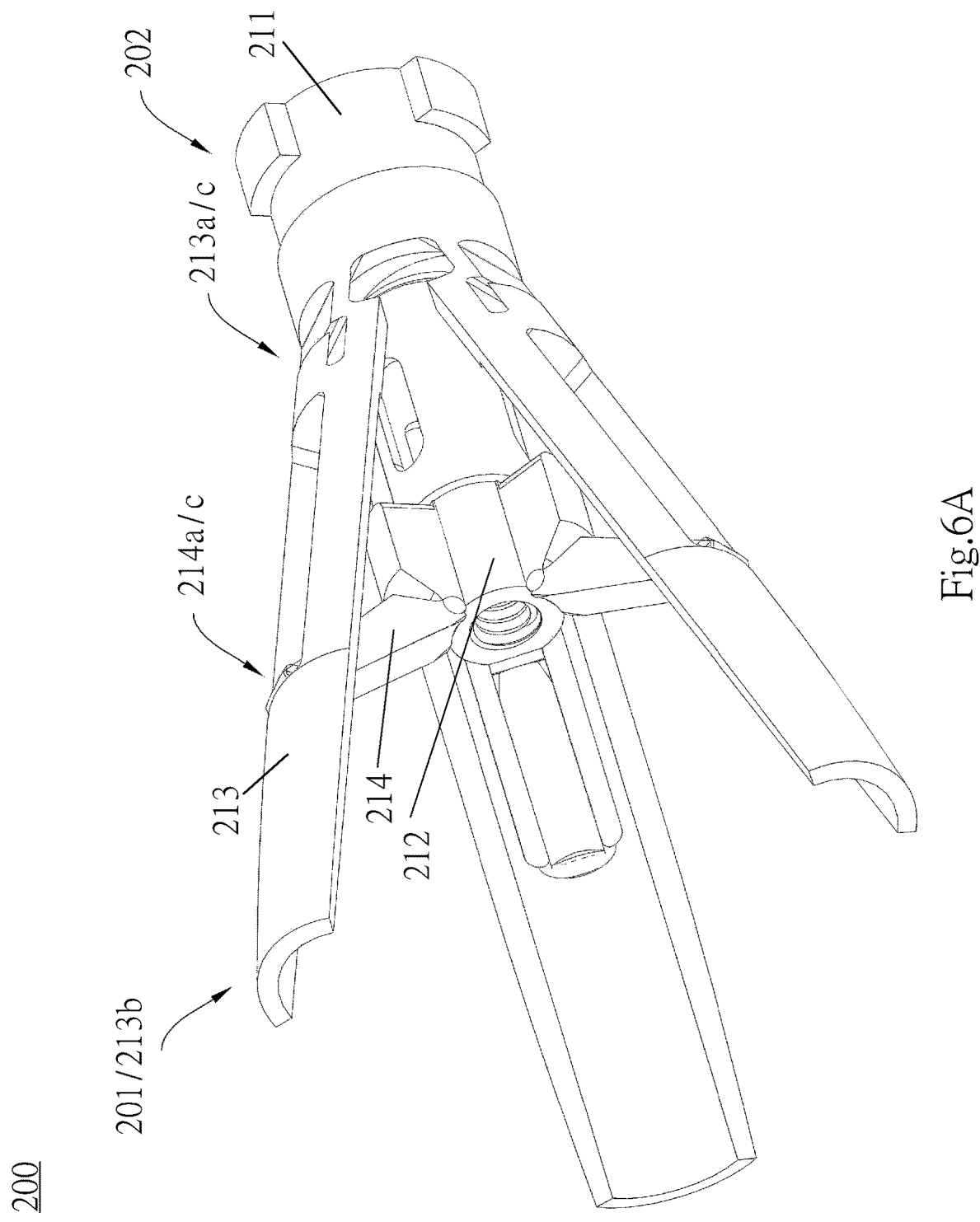
Figure 6B:
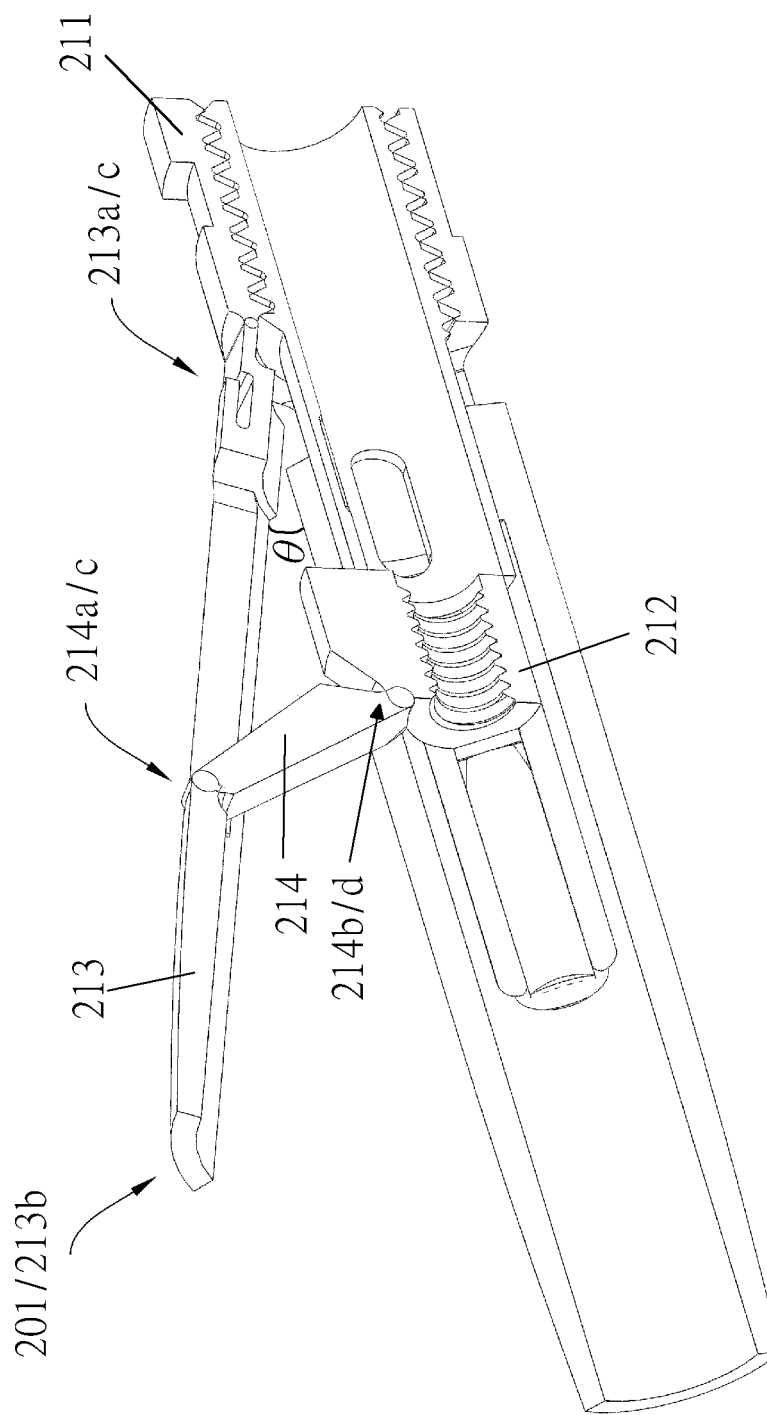

FIG. 5A and FIG. 5B are a lateral view and a cross-sectional view of the spinal implant structure 200 which is folded, respectively. FIG. 6A through FIG. 6C are a lateral view, a cross-sectional view, and a front view of the spinal implant structure 200 which has been expanded, respectively. Referring to FIGS. 5A, 5B, 6A, 6B, the spinal implant structure 200 comprises a body 210 and a fixing screw barrel 220. When the spinal implant structure 200 is folded, the body 210 is a hollow-cored cylinder, and the fixing screw barrel 220 is also a hollow-cored cylinder. The spinal implant structure 200 has an expansion end 201 (left end) and a fixing end 202 (right end). The expansion end 201 is expanded with the operating tool (shown in FIG. 5A and FIG. 6A), and the degree of expansion can be adjusted as needed.

[Body]

The body 210 of the spinal implant structure 200 comprises a first part 211, a second part 212, an expansion arm 213 and a support arm 214, and the four parts are integrally formed. Both the first part 211 and the second part 212 are hollow-cored cylinders. The first part 211 and the second part 212, which are separated and do not overlap, are arranged along the same horizontal axis (X-axis). That is, the first part 211 and the second part 212 can be considered as two smaller independent tubes split from the body 210, and the two parts are connected by the expansion arm 213 and the support arm 214. The first part 211 contains the fixing screw barrel 220. The second part 212 contains a netting 230 and a fixing component 240 (FIG. 6A through FIG. 8B). The first part 211 has an internal diameter slightly larger than that of the second part 212. When the spinal implant structure 200 is folded, the distance between the first part 211 and the second part 212 is very short or the two parts even meet each other. The degree of the expansion of the spinal implant structure 200 can be changed by adjusting the distance between the first part 211 and the second part 212. The second embodiment differs from the first embodiment in that when the first part 211 and the second part 212 move away from each other, that is, the distance between the first part 211 and the second part 212 along the horizontal axis (X-axis) increases, the degree of expansion increases. In view of this, an operating tool (a central rod, to be described later) is required to move the second part 212 toward the expansion end 201 (i.e., leftward), so as to expand the spinal implant structure 200.

The spinal implant structure 200 is expanded because of the bending of the expansion arm 213. The expansion arm 213 has an end 213a (first end) which connects with the first part 211 and extends outward from the first part 211. The other end 213b (second end) of the expansion arm 213 is a free end which does not connect with any other component. A stress weakening portion (weakened section) is defined at a junction 213c of the expansion arm 213 and the first part 211. The stress weakening portion is, for example, made thin or hollowed out so that the stress weakening portion (weakened section) is weaker than its surroundings. When subjected to an applied force, the expansion arm 213 bends outward from the stress weakening portion to effectuate expansion. An included angle θ (FIG. 6B) smaller than 90 degrees is formed between the expansion arm 213 and the extension line of the first part 211. The included angle θ indicates the degree of the expansion of the spinal implant structure 200. The included angle θ equals 0 degree when the spinal implant structure 200 is folded (FIG. 5A and FIG. 5B). The included angle θ is larger than 0 degree but smaller than 90 degrees when the spinal implant structure 200 has been expanded (FIG. 6A and FIG. 6B). The expansion arm 213 is in the number of one or more. If the expansion arm 213 is in the number of two or more, the expansion arms 213 connected to the first part 211 are equally spaced apart. As shown in FIG. 6C, the spinal implant structure 200 comprises three expansion arms 213 spaced apart by 120 degrees. In another embodiment of the present invention, the expansion arms are in the number of two (and thus spaced apart by 180 degrees), four (and thus spaced apart by 90 degrees) or more. The more the expansion arms are provided, the more uniform the distribution of forces required to effectuate expansion is, the smaller each expansion arm is, and the stricter the requirement for product precision is.

The expansion arm 213 has therein a support arm 214. The support arm 214 is tongue-like in shape and can be considered as formed by being split from the expansion arm 213; in other words, the support arm 214 and the expansion arm 213 are formed integrally. On the other hand, the expansion arm 213 and the support arm 214 can both be considered as being split from the body 210. An end 214a (first end) of the support arm 214 is not only connected to the inner side of the expansion arm 213, but also connected to the expansion arm 213 in a manner to be positioned proximate to the free end 213b. The other end 214b (second end) of the support arm 214 is connected to the second part 112 in a manner to be positioned distal to the first part 211. At least one stress weakening portion (weakened region) is defined at the support arm 214. This embodiment is exemplified by two stress weakening portions located at a junction 214c of the support arm 214 and the expansion arm 213 and a junction 214d of the support arm 214 and the second part 212, respectively. In response to an increase in the distance between the first part 211 and the second part 212, the support arm 214 bends at the stress weakening portions under a force. As shown in FIG. 6B, at the stress weakening portion 214c, the support arm 214 bends toward the inner side of the spinal implant structure 200, whereas, at the stress weakening portion 214d, the support arm 214 bends toward the outer side of the spinal implant structure 200, thereby driving the expansion arm 213 to bend toward the outer side of the spinal implant structure 200 and thus increasing the included angle θ, so as for the spinal implant structure 200 to expand. The stress weakening portions are, for example, made thin or hollowed out so that the stress weakening portions are weaker than their surroundings; hence, when the support arm 214 is subjected to an applied force, the resultant stress is concentrated on the stress weakening portions, thereby causing structural deformation of the support arm 214 (i.e., the bending of the support arm 214).

[Derivative Design of the Body]

Figure 21A:
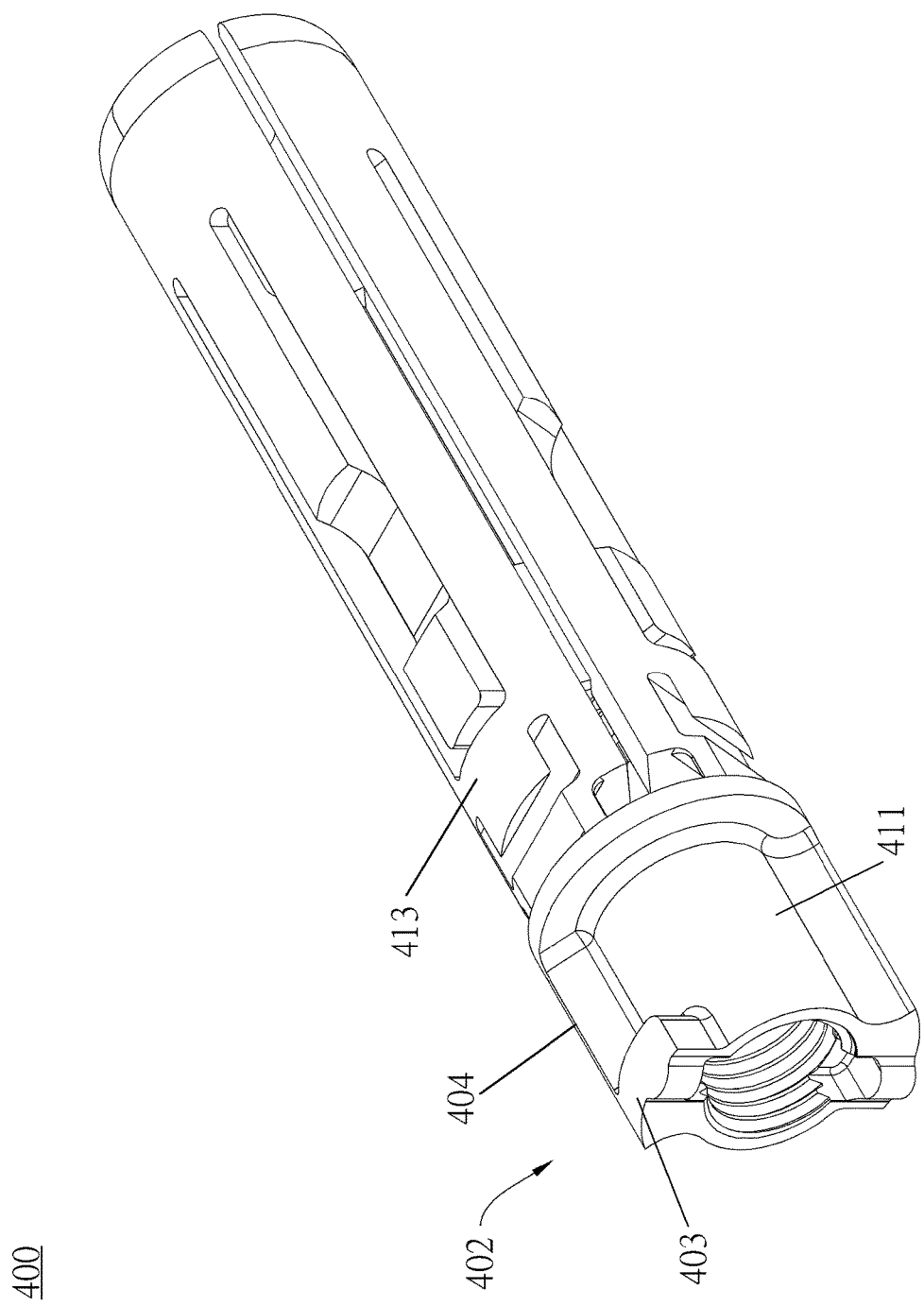
FIG. 21A through FIG. 21B are schematic views of the spinal implant structure according to yet another embodiment of the present invention.
Figure 21B:
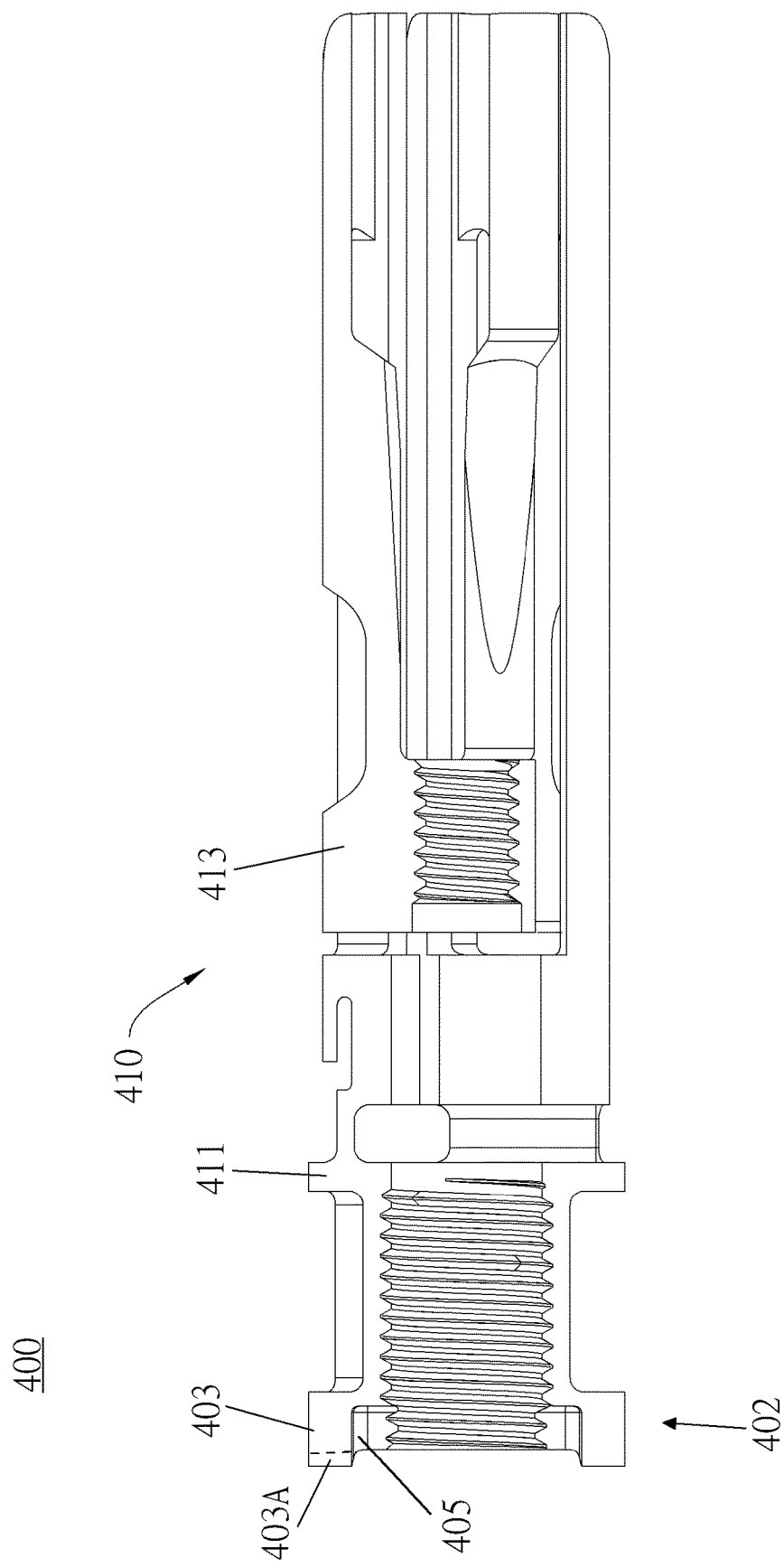

Referring to FIG. 21A and FIG. 21B, which illustrate a spinal implant structure 400 according to yet another embodiment of this invention. The difference between the spinal implant structure 400 and the above-described spinal implant structure 200 lies in the design of a fixing end 402.

As shown in FIG. 21A, an engagement positioning block 403 (the same design as in the spinal implant structure 200) is provided at the fixing end 402 (the left end) of the spinal implant structure 400, and is used to engage an operating tool described below. A corresponding engaging slot is provided at an engaging end of the operating tool for engaging the spinal implant structure 400. An extension rib 404 is also provided on the spinal implant structure 400 and extends from the engagement positioning block 403 toward the inner side of the spinal implant structure 400 (i.e., toward the expansion arm 413). The extension rib 404 is used for enhancing the strength of the first part 411 of the spinal implant structure 400, so that structural distortion or fracture can be avoided during the implanting process. Besides, as shown in FIG. 21B, the engagement positioning block 403 can extend slightly more toward the outer (left) side of the spinal implant structure 400 and have an extra outer protruding block 403A extending out from the fixing end 402 of the spinal implant structure 400. When the spinal implant structure 400 comprises the outer protruding block 403A, it can more steadily connect with or engage an operating tool (as will be described later) having a corresponding slot or recess structure, and the occurrence of sliding or displacement in the implanting process can be reduced. In yet another embodiment of this invention, a recess 405 can be arranged at the inner side of a body 410 of the spinal implant structure 400. The recess 405 connects to the outside of the body 410, and has an opening in a horizontal direction (X-axis) of the first part 411. The recess 405 can be a long concaved slot or groove, and as the recess 405 has one opening end and another closed end, an auxiliary tool (such as a long and thin rod or needle) can be used to reach into the recess 405 from the outside of the body 410 to further apply a force by pressing against the recess 405. As such, when withdrawing the operating tool, the force applying thereto can be increased without causing displacement of the spinal implant structure 400, thereby solving the problem of distortion during the implanting process that hampers withdrawal of the operating tool.

[Fixing Screw Barrel]

Like the body 210, the fixing screw barrel 220 is a hollow-cored cylinder. The fixing screw barrel 220 fixes the distance between the first part 211 and the second part 212 upon completion of the expansion of the spinal implant structure 200. The fixing screw barrel 220 has a smaller diameter than the first part 211 so as to fit inside the first part 211. A third outer thread is disposed on a portion of the outer surface of the fixing screw barrel 220. The third outer thread matches a third inner thread disposed on the inner surface of the first part 211. Hence, the fixing screw barrel 220 can be rotated and inserted into the first part 211, so as to be adjustably moved forward and backward by the threads and fixed in place. Since the position of the fixing screw barrel 220 is adjustable, the front end of the fixing screw barrel 220 can abuttingly connect with the second part 212 so that the second part 212 is fixed in place, thereby fixing the distance between the first part 211 and the second part 212. Since the fixing screw barrel 220 is adjustably moved forward and backward by the threads, it generates a torque. As a result, the spinal implant structure 200 in operation does not require the fixing screw barrel 220 to move the second part 212; instead, a central rod (to be described later) of the operating tool moves the second part 212 horizontally away from the first part 211 and thus effectuates the expansion of the spinal implant structure 200, and then the fixing screw barrel 220 is moved forward to abuttingly connect with the second part 212, thereby fixing the second part 212 in place.

Referring to FIG. 5B, when the spinal implant structure 200 is folded, the tail of the fixing screw barrel 220 protrudes from the first part 211 slightly. Referring to FIG. 6B, when the spinal implant structure 200 has been expanded, the second part 212 separates from the first part 211 to allow the tail of the fixing screw barrel 220 to enter the first part 211 completely and allow the front end of the fixing screw barrel 220 to abuttingly connect with the second part 211, thereby fixing the distance between the first part 211 and the second part 212.

The wall of the fixing screw barrel 220 has one or at least two through holes 222 whereby the bone cement enters the vertebral body during the bone cement perfusion step (to be described later).

[Netting]

Figure 7A:
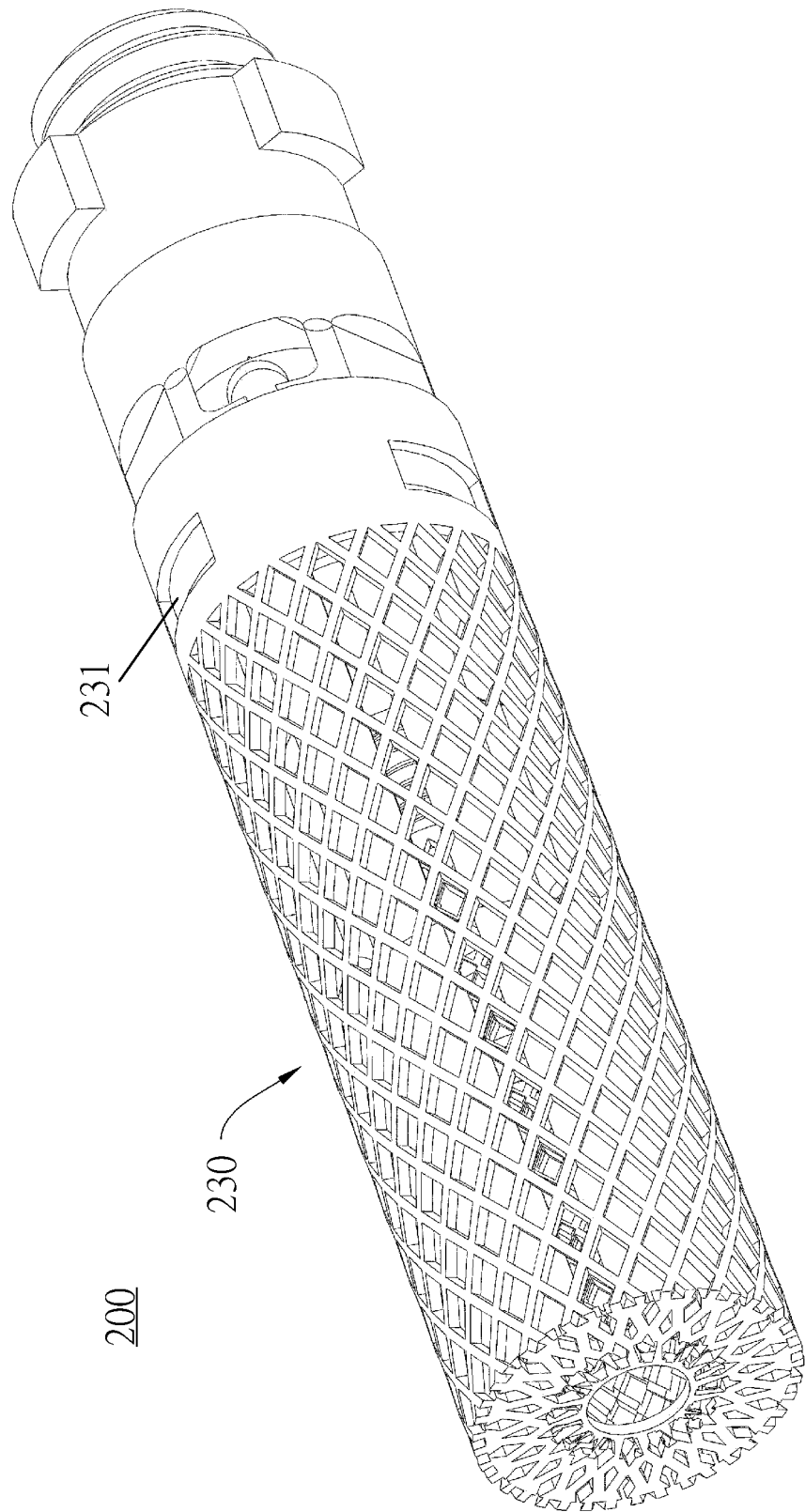
FIG. 7A and FIG. 7B show that the spinal implant structure (i.e., netted) is folded.
Figure 7B:
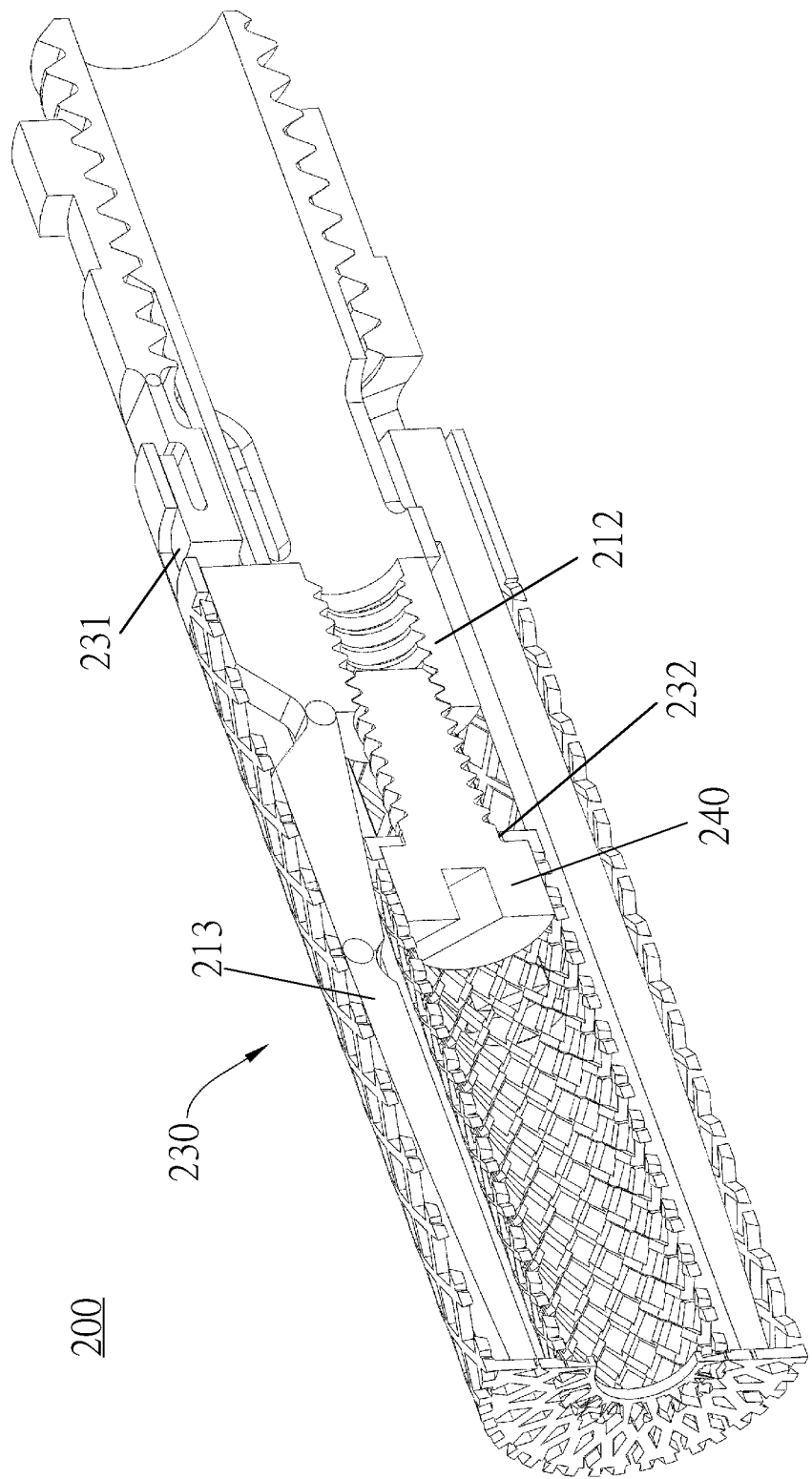
Figure 8A:
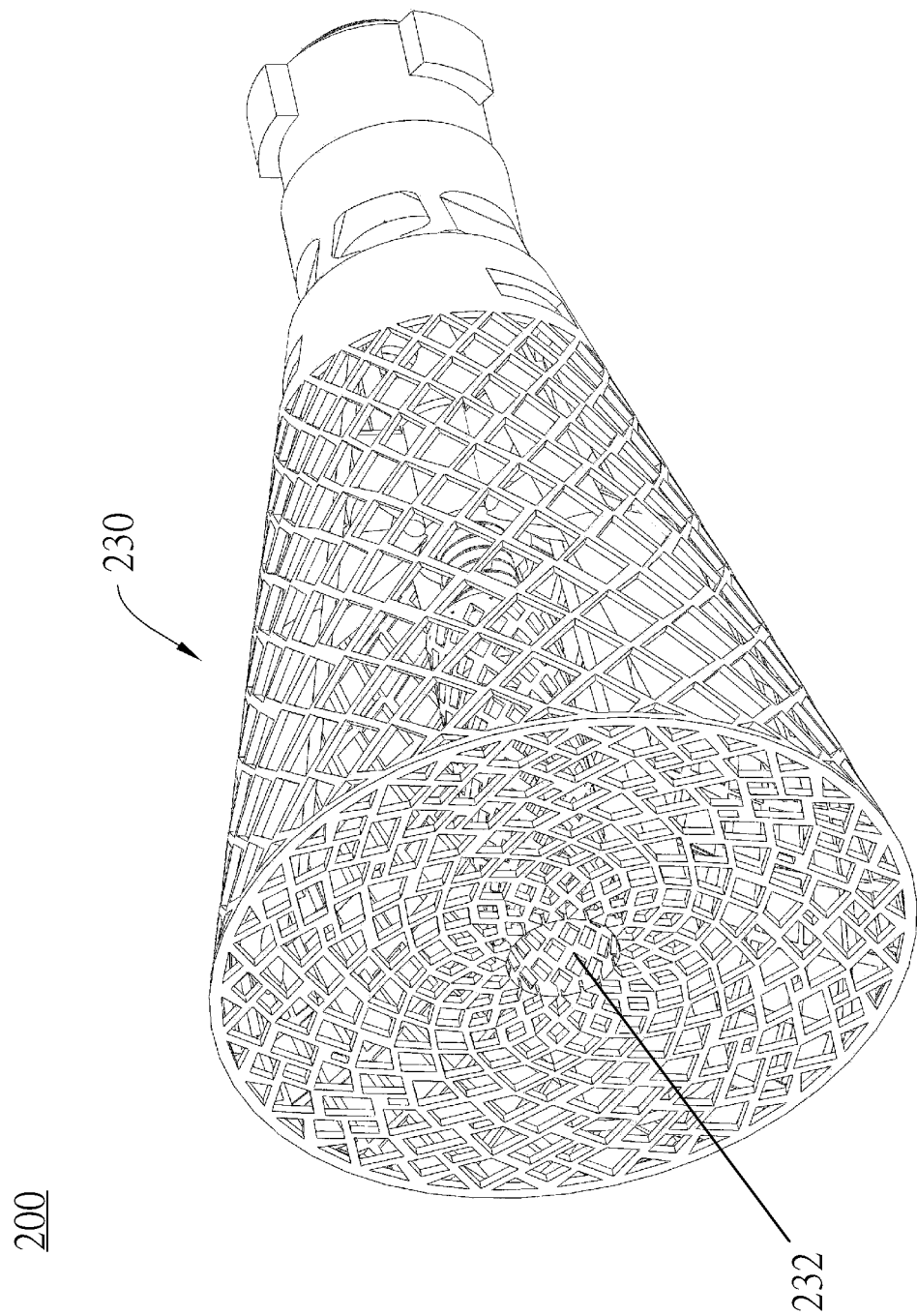
Figure 8B:
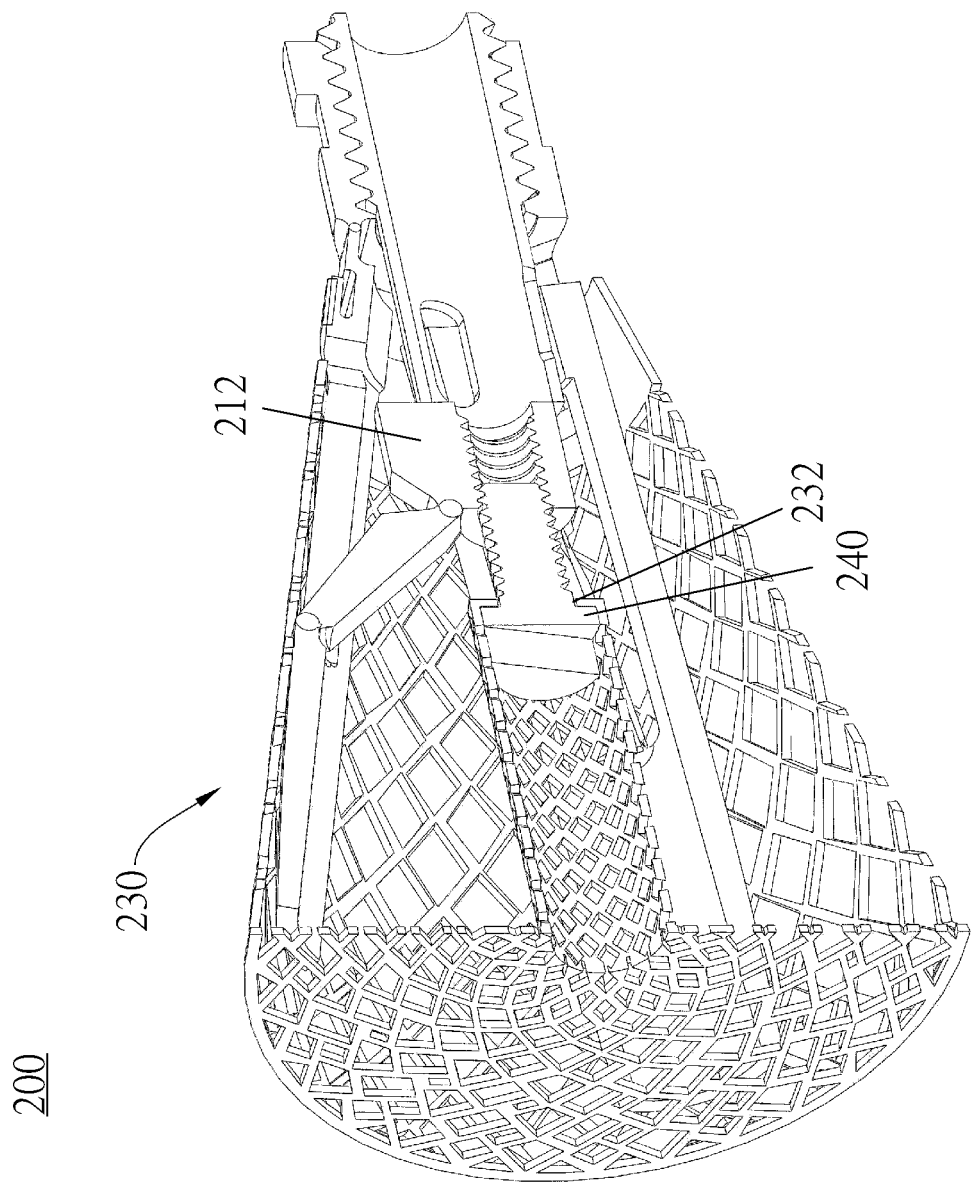

FIG. 7A through FIG. 8B show that the spinal implant structure 200 has a netting 230 mounted thereon. FIG. 7A and FIG. 7B show that the spinal implant structure 200 is folded. FIG. 8A and FIG. 8B show that the spinal implant structure 200 has been expanded. The netting 230 restricts the range of flow of the bone cement being perfused into the spinal implant structure 200, so as to prevent the bone cement from spilling from the vertebral body, allow the spinal implant structure 200 to be uniformly expanded, and reinforce the vertebral body.

The netting 230 is hollow-cored and cylindrical in shape. The netting 230 fits around the expansion arm 213 of the spinal implant structure 200 and can unfold as a result of the expansion of the spinal implant structure 200 (FIG. 8B). The openings at the two ends of the netting 230 differ in size. The sidewall of the end with a larger opening has at least one engaging hole 231. The end is engaged with a first part-facing end of the expansion arm 213. The other end of the netting 230 has a fixing hole 232 of a smaller diameter (FIG. 8A). When the spinal implant structure 200 is folded (FIG. 7B), one end of the netting 230 is fixed to the expansion arm 213 through the engaging hole 231, whereas the other end of the netting 230 is bent to be inserted into the spinal implant structure 200, and in consequence the fixing component 240 is fixed to the second part 212 through the fixing hole 232. The fixing component 240 is, for example, a screw whose thread enables it to be rotated and inserted into the second part 212. The outer diameter of the screw's head is slightly larger than the diameter of the fixing hole 232 of the netting 230. Hence, the netting 230 is fixed in place between the screw's head and thread; in other words, the netting 230 is fixed in place at the junction of the fixing component 240 and the second part 212. The second embodiment differs from the first embodiment in that the netting 230 of the spinal implant structure 200 is steadily engaged between the fixing component 240 and the second part 212 without getting disconnected, and thus when the spinal implant structure 200 is expanded (FIGS. 8A, 8B), that is, at the time when the second part 212 moves toward the expansion end 101 under a pushing force and thus moves away from the first part 211, the netting 230 unfolds as a result of the expansion of the spinal implant structure 200.

Operating Tool

The spinal implant structure of the present invention operates in conjunction with an operating tool in order to perform precise operations, such as implantation, expansion, and bone cement perfusion. Embodiments of the operating tool of the present invention are illustrated by FIG. 9A through FIG. 20C. FIG. 9A through FIG. 15A are schematic views of the operating tool. FIG. 16A through FIG. 18B are schematic views of the operating tool and the spinal implant structure coupled thereto according to the first embodiment. FIG. 19A through FIG. 20C are schematic views of the operating tool and the spinal implant structure coupled thereto according to the second embodiment. FIG. 9A through FIG. 15A show that, although the operating tool connects with the spinal implant structure 100, the operating tool is also applicable to the spinal implant structure 200 in part or in full. Persons skilled in the art understand that although the operating tool of the present invention varies slightly in structure and shape, depending on whether it is applied to the spinal implant structure 100 or the spinal implant structure 200, the variations in structure and shape of the operating tool are designed in accordance with operational concepts and relationships disclosed according to the present invention and thus fall within the scope of the present invention.

Referring to FIG. 9A through 15A, the operating tool of the present invention comprises a tool body 310, a fixing (screw barrel/screw nut) sleeve 320, a central rod 330, an operating handle 340, a converter 350, a bone cement perfusing sleeve 360, and a bone cement ejector 370. The tool body 310, fixing (screw barrel/screw nut) sleeve 320, the central rod 330, operating handle 340, and converter 350 together constitute the operating tool whereby the spinal implant structure is expanded (FIG. 16A through FIG. 17C show how the spinal implant structure 100 is folded/expanded; FIG. 19A through FIG. 20C show how the spinal implant structure 200 is folded/expanded.) The tool body 310, fixing (screw barrel/screw nut) sleeve 320, bone cement perfusing sleeve 360, and bone cement ejector 370 together constitute the tool for perfusing the bone cement upon completion of the expansion of the spinal implant structure 100 (FIGS. 18A and 18B).

[Tool Body]

Figure 9B:
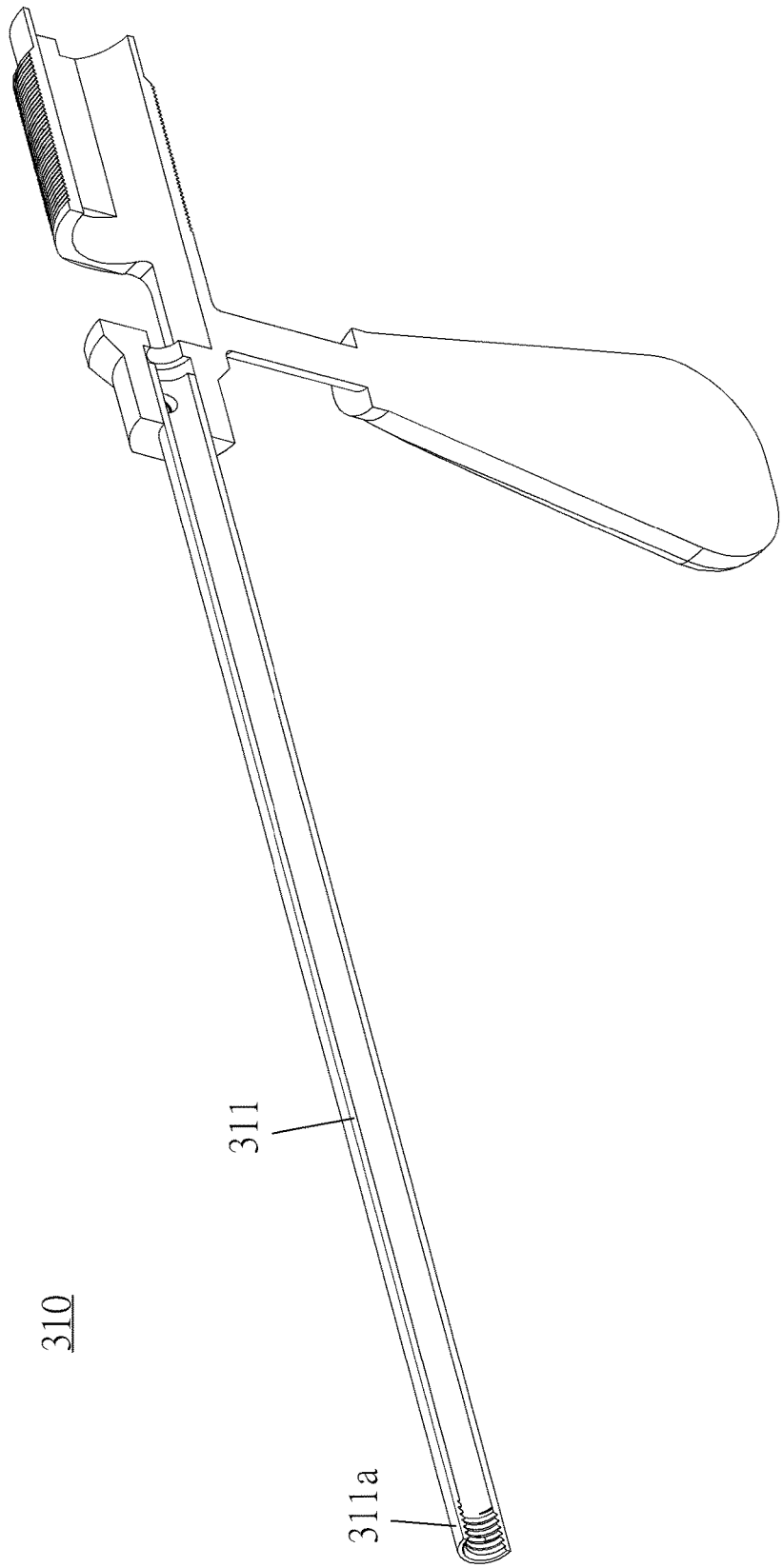

Referring to FIGS. 9A and 9B, the tool body 310 serves as a carrier/connector for the operating tool and connects with the spinal implant structure 100. The tool body 310 comprises a connecting portion 311 and a gripping portion 312. The connecting portion 311 is a hollow-cored pipe and has a tail 311a. The tail 311a has a jointing structure which can be connected to the spinal implant structure 100 and fixed thereto integrally. This embodiment is exemplified by thread securing. The ways to couple the tool body 310 and the spinal implant structure 100 together include but are not limited to engagement and thread securing; hence, whatever jointing techniques will be applicable to the present invention, provided that the jointing techniques enable the tool body 310 and the spinal implant structure 100 to be firmly connected and easily disconnected. The gripping portion 312 is, for example, a handle to be gripped by a user or placed on another table/support to fix the kit in place.

[Fixing (Screw Barrel/Screw Nut) Sleeve]

Figure 10A:
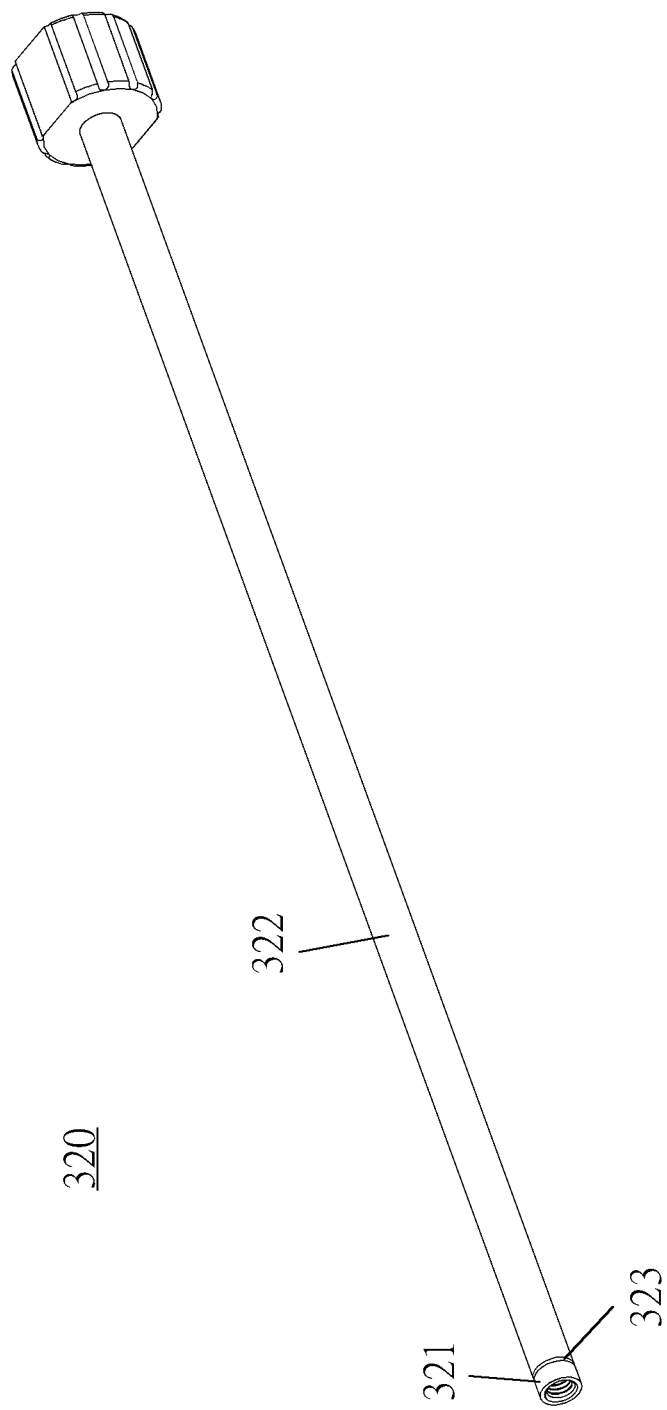
Figure 10B:
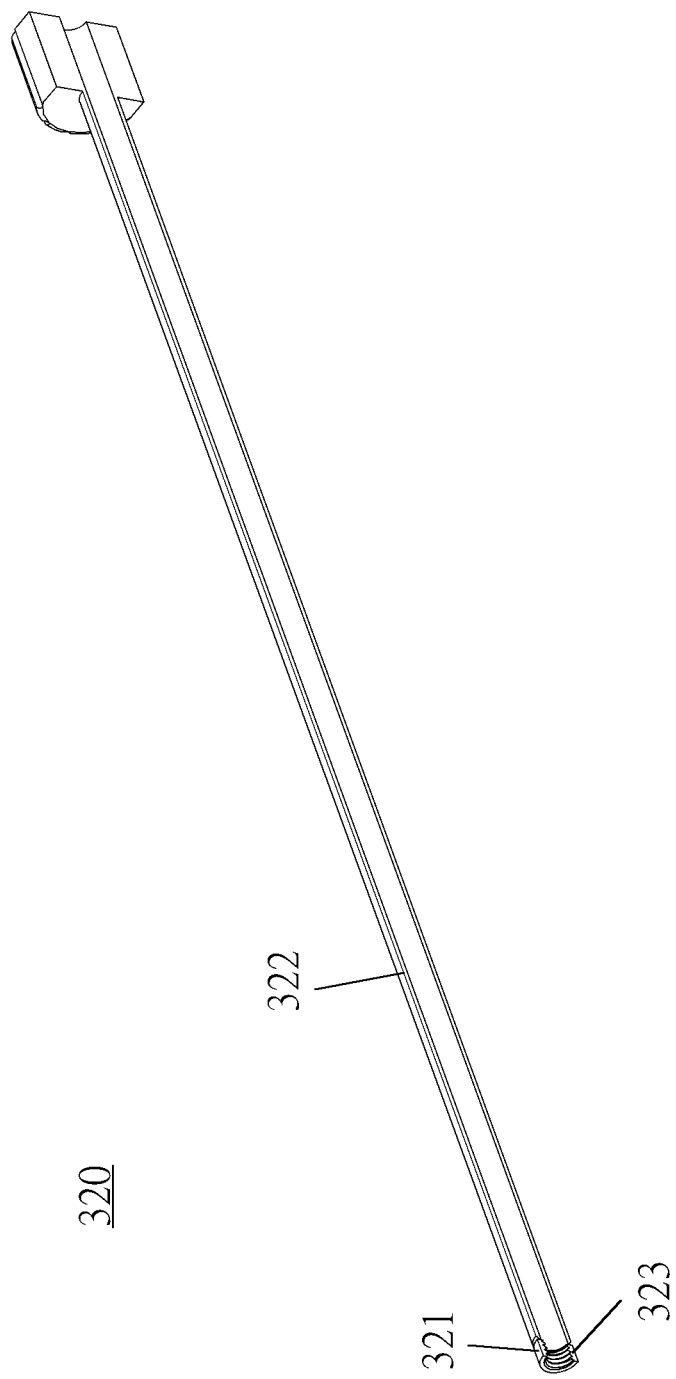
Figure 10C:
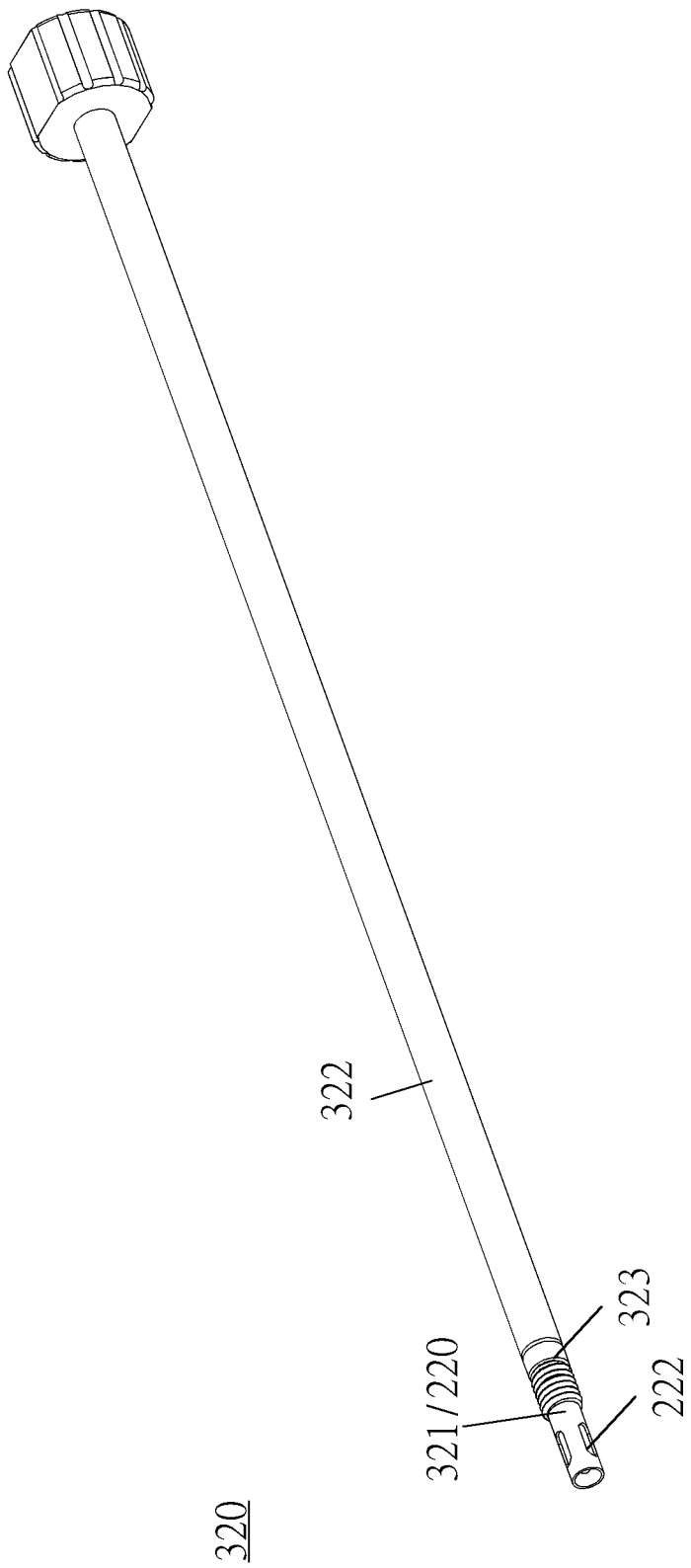

Referring to FIG. 10A through FIG. 10C, wherein FIG. 10A and FIG. 10B show the fixing (screw barrel/screw nut) sleeve 320 which operates in conjunction with the spinal implant structure 100, and FIG. 10C shows the fixing (screw barrel/screw nut) sleeve 320 which operates in conjunction with the spinal implant structure 200. The fixing (screw barrel/screw nut) sleeve 320 is a hollow-cored pipe for fitting inside the tool body 310. For example, the fixing (screw barrel/screw nut) sleeve 320 comprises a fixing screw barrel/screw nut 321 and a sleeve 322. The fixing screw barrel/screw nut 321 is specially designed (for example, its wall has an opening 323) to separate from the sleeve 322 when rotated and stay in the spinal implant structure 100, and then the sleeve 322 can be taken out of the spinal implant structure 100. Referring to FIG. 10A, the fixing screw nut 321 is disconnected from the fixing (screw barrel/screw nut) sleeve 320 to become a screw nut (i.e., a screw nut for fitting around a protruding part of the fixing screw barrel 120, as described before and shown in FIG. 1B) of the spinal implant structure 100 in the first embodiment. Referring to FIG. 10C, the fixing screw barrel 321 is disconnected from the fixing (screw barrel/screw nut) sleeve 320 to become the fixing screw barrel 220 (FIG. 5B) of the spinal implant structure 200 in the second embodiment. The fixing (screw nut/screw barrel) 321 disconnected from the fixing (screw barrel/screw nut) sleeve 320 is adapted to fix the distance between the first part 111, 211 and the second part 112, 212 in the spinal implant structure 100, 200.

[Central Rod]

Figure 11A:
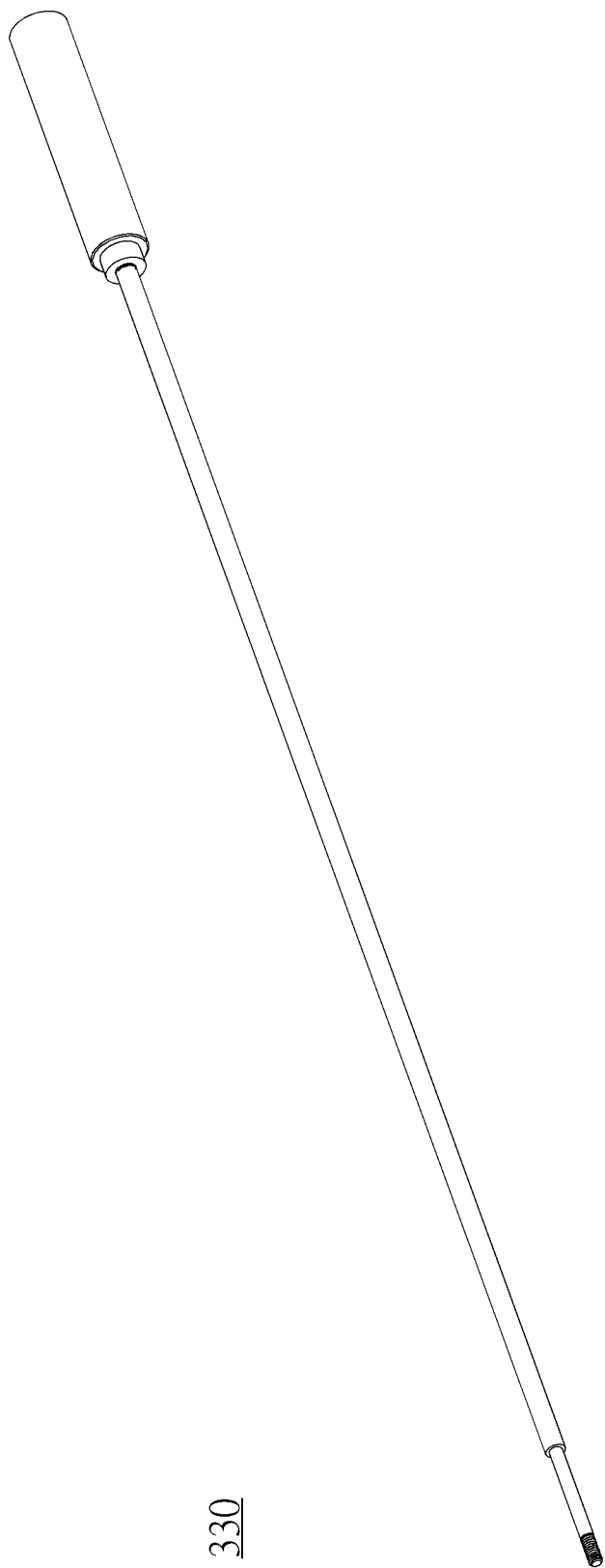
Figure 11B:
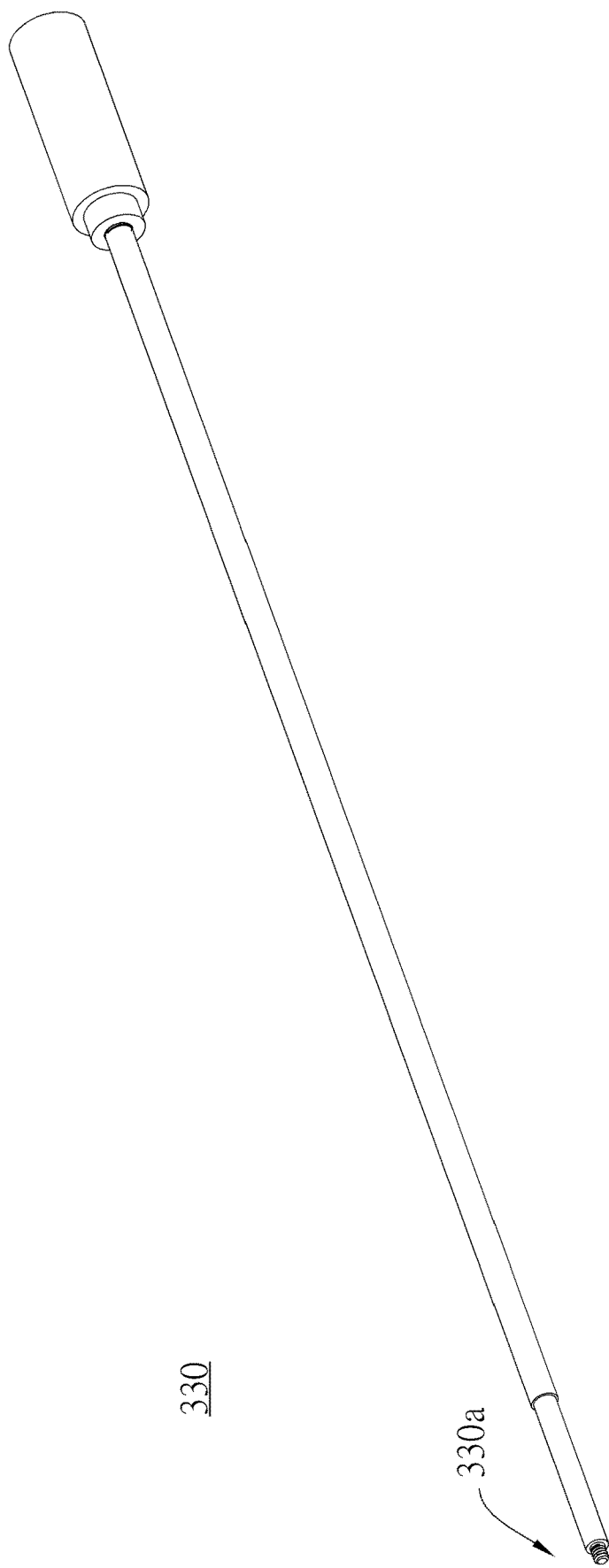
Figure 12A:
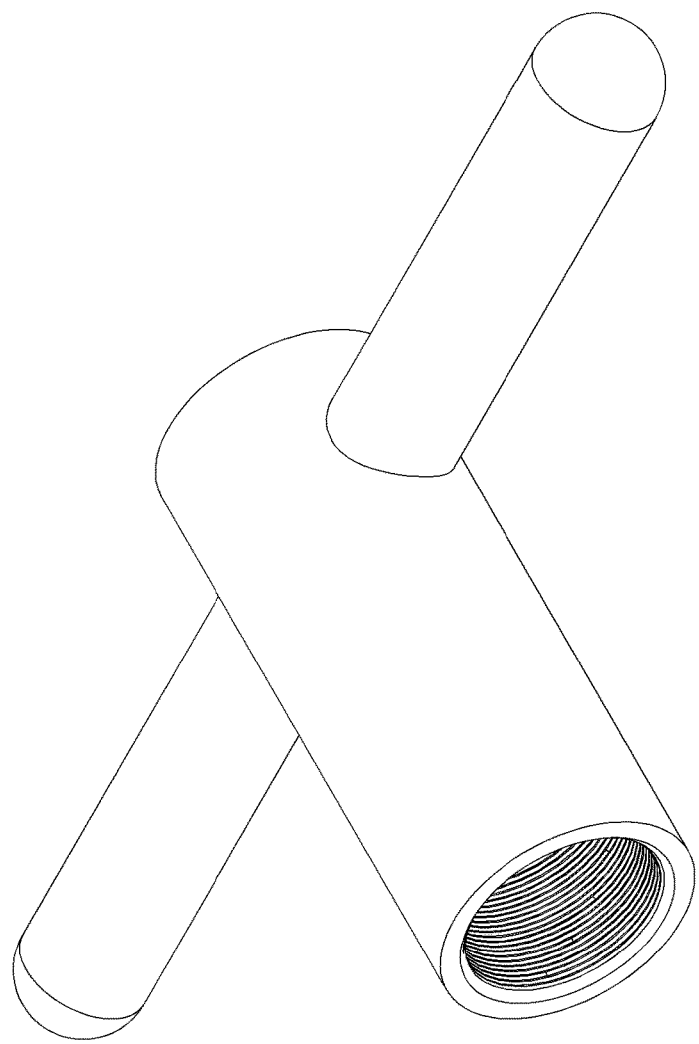
Figure 12B:
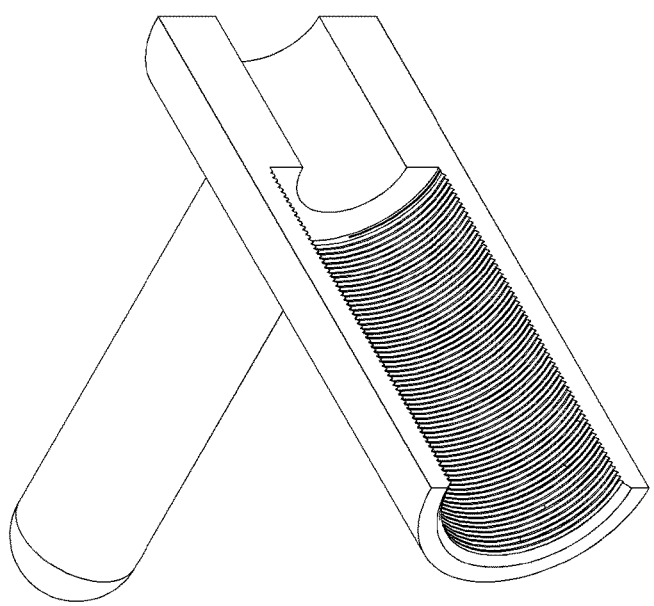
Figure 13A:
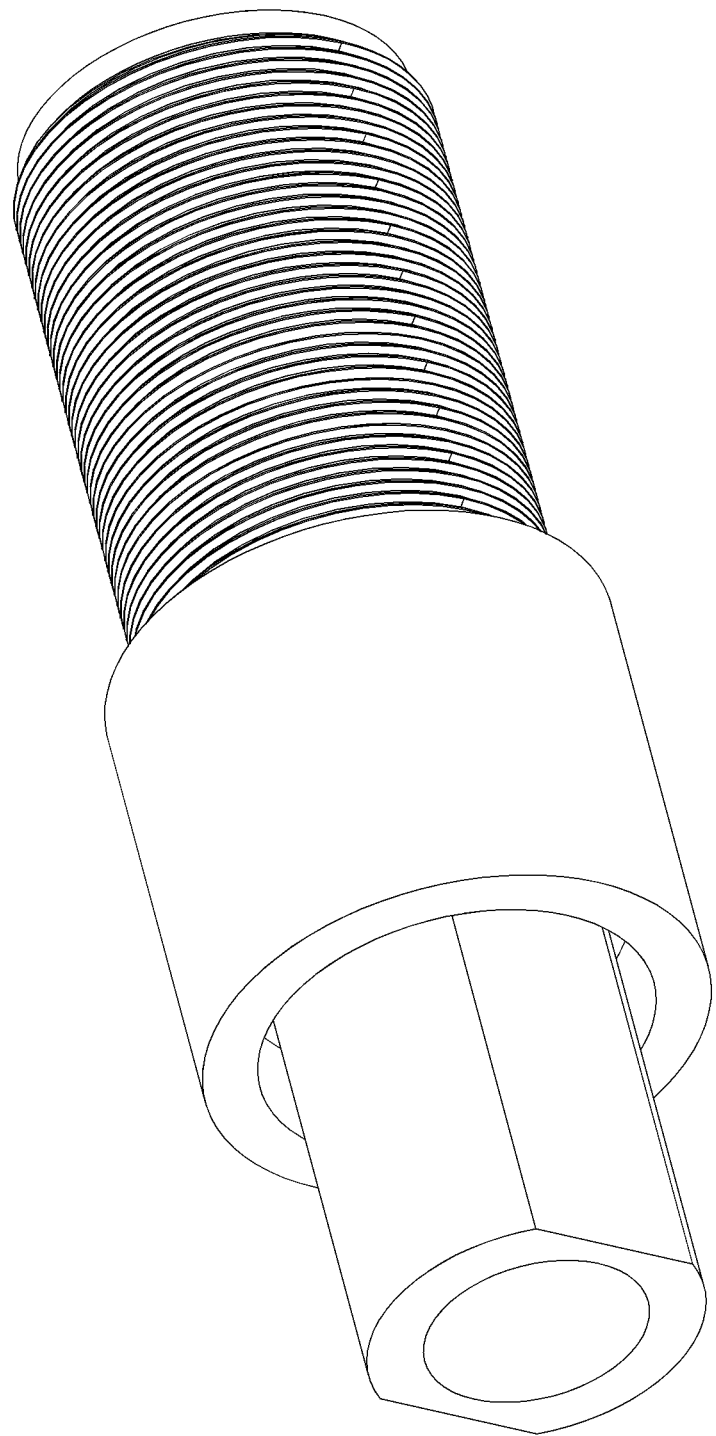
Figure 13B:
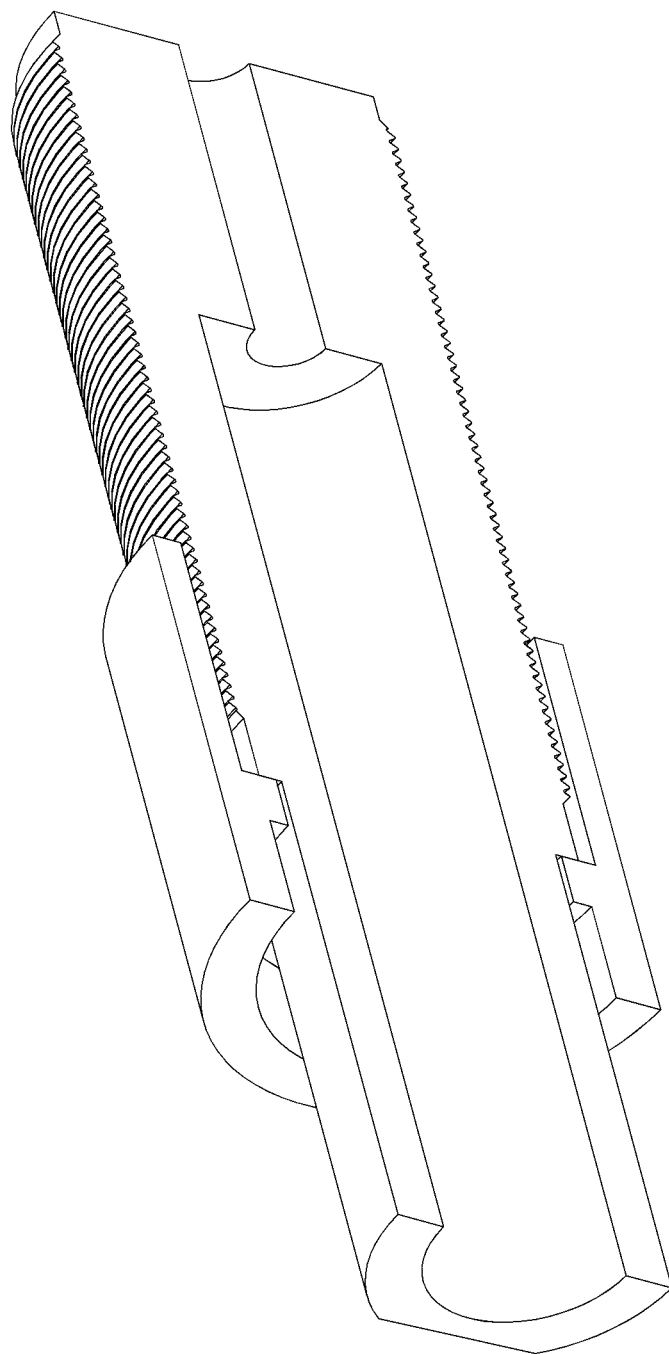
Figure 14A:
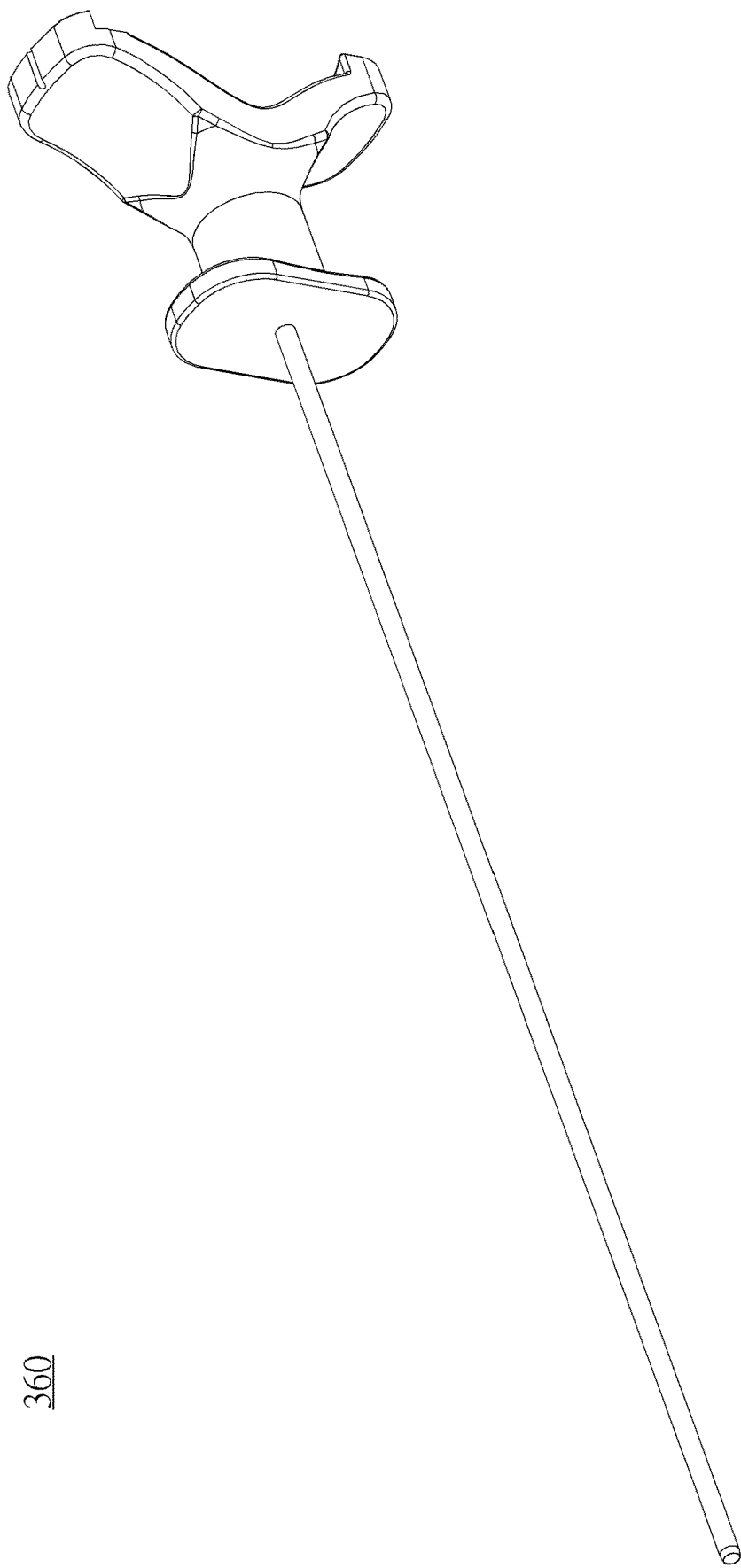
Figure 14B:
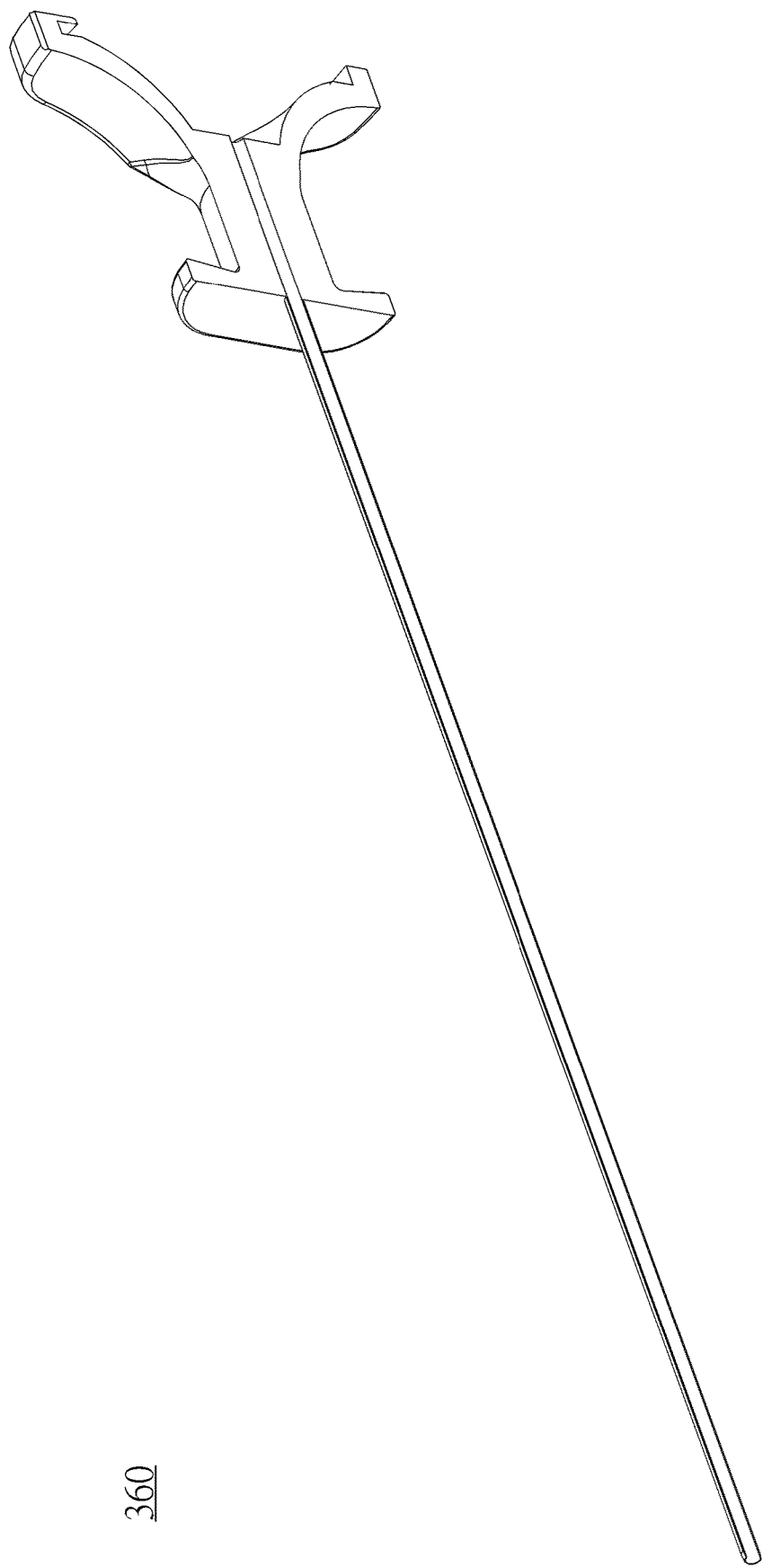
Figure 15A:
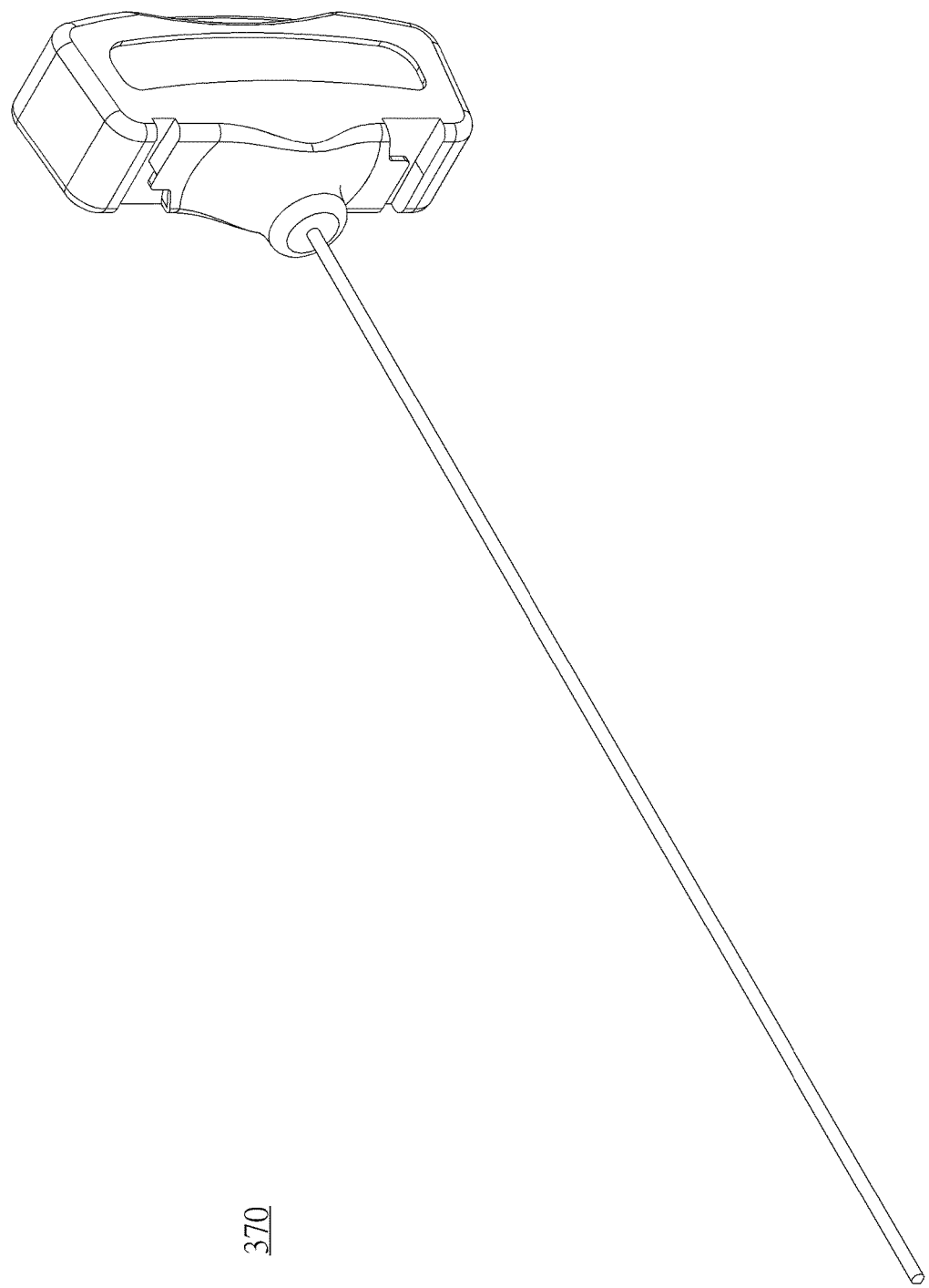

Referring to FIGS. 11A and 11B, wherein FIG. 11A shows a central rod for use with the spinal implant structure 100, and FIG. 11B shows a central rod adapted for use with the spinal implant structure 100 and equipped with a connecting end 330a (left end). The central rod 330 is a slender rod for pulling and/or pushing the second part so as to effectuate the expansion of the spinal implant structure. The front end of the central rod 330 has a thread which matches the inner thread of the fixing screw barrel 120 of the spinal implant structure 100; hence, the front end of the central rod 330 can be insertedly fastened to the fixing screw barrel 120 and thus connected to the second part 112 of the spinal implant structure 100 through the fixing screw barrel 120 (as shown in FIG. 1B). Alternatively, the thread matches the inner thread of the second part 212 of the spinal implant structure 200 and thus is directly, insertedly fastened to the second part 212 of the spinal implant structure 200 (as shown in FIG. 5B).

[Operating Handle and Converter]

Referring to FIG. 12A through 13B, the operating handle 340 and the converter 350 drive the central rod 330 to move forward/backward so that the spinal implant structures 100, 200 are expanded or folded. The operating handle 340 operates by the principle of the lever whereby the user can exert a small force on the converter 350 by means of a long effort arm of the lever. The converter 350 converts the rotational torque exerted by the user into a horizontal, linear pushing/pulling force, so as to not only render the pushing/pulling force uniform but also reduce unnecessary vibration.

[Bone Cement Perfusing Sleeve and Bone Cement Ejector]

Referring to FIG. 14A through 15A, the bone cement perfusing sleeve 360 and the bone cement ejector 370 are adapted to perfuse a bone cement, and their operation is illustrated by FIGS. 19)18B, which show that their operation entails inserting the bone cement perfusing sleeve 360 directly into the fixing screw barrel (screw nut) 320, the tool body 310, and the spinal implant structure 100, filling the bone cement perfusing sleeve 360 with the bone cement, and finally pushing the bone cement into the spinal implant structure 100 with the bone cement ejector 370. Hence, the outer diameter of the bone cement ejector 370 substantially equals the inner diameter of the bone cement perfusing sleeve 360 in order for the bone cement to be pushed into the spinal implant structure 100.

[Operation of Operating Tool and Spinal Implant Structure]

Figure 16A:
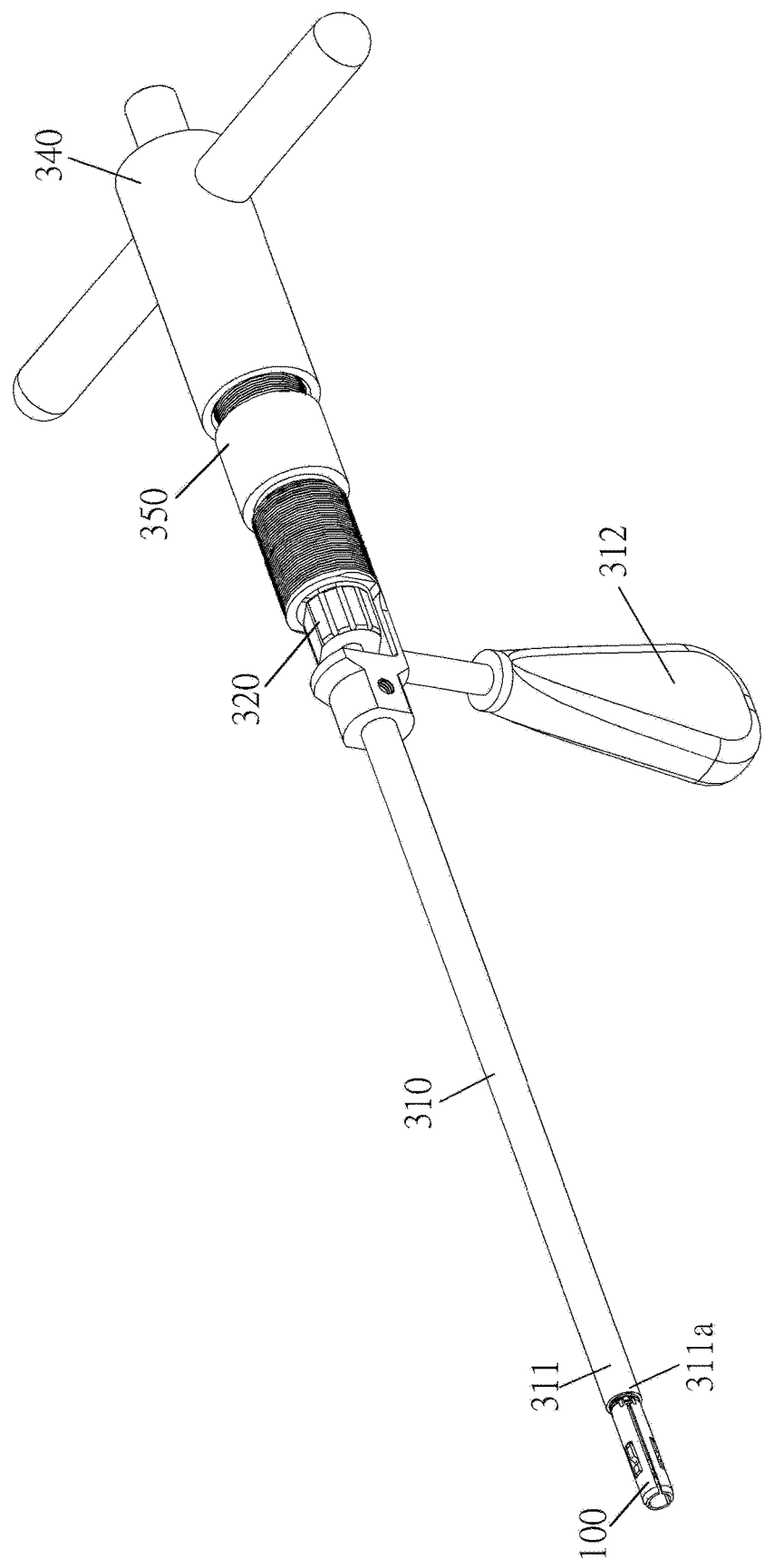
Figure 16B:
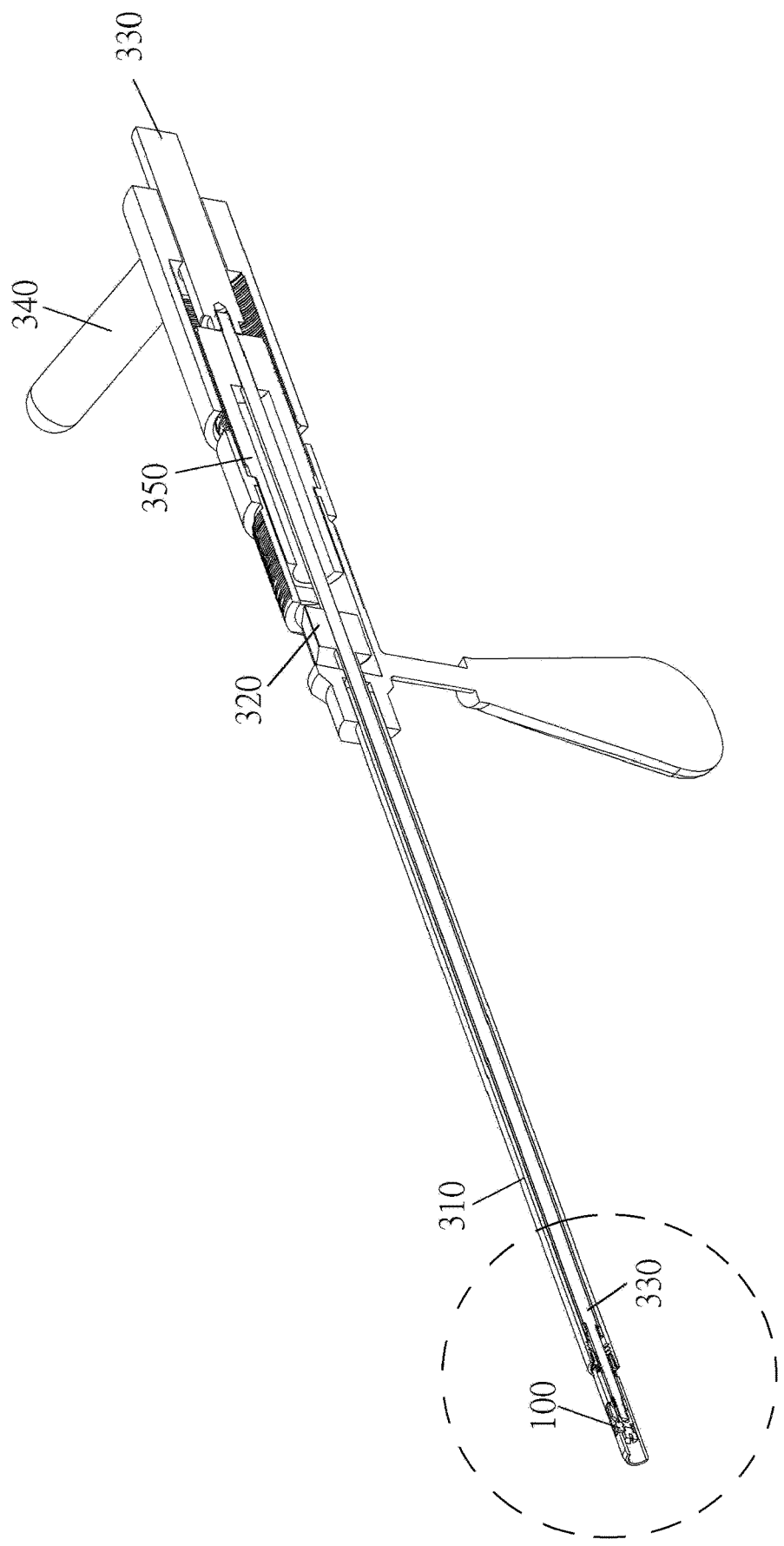
Figure 16C:
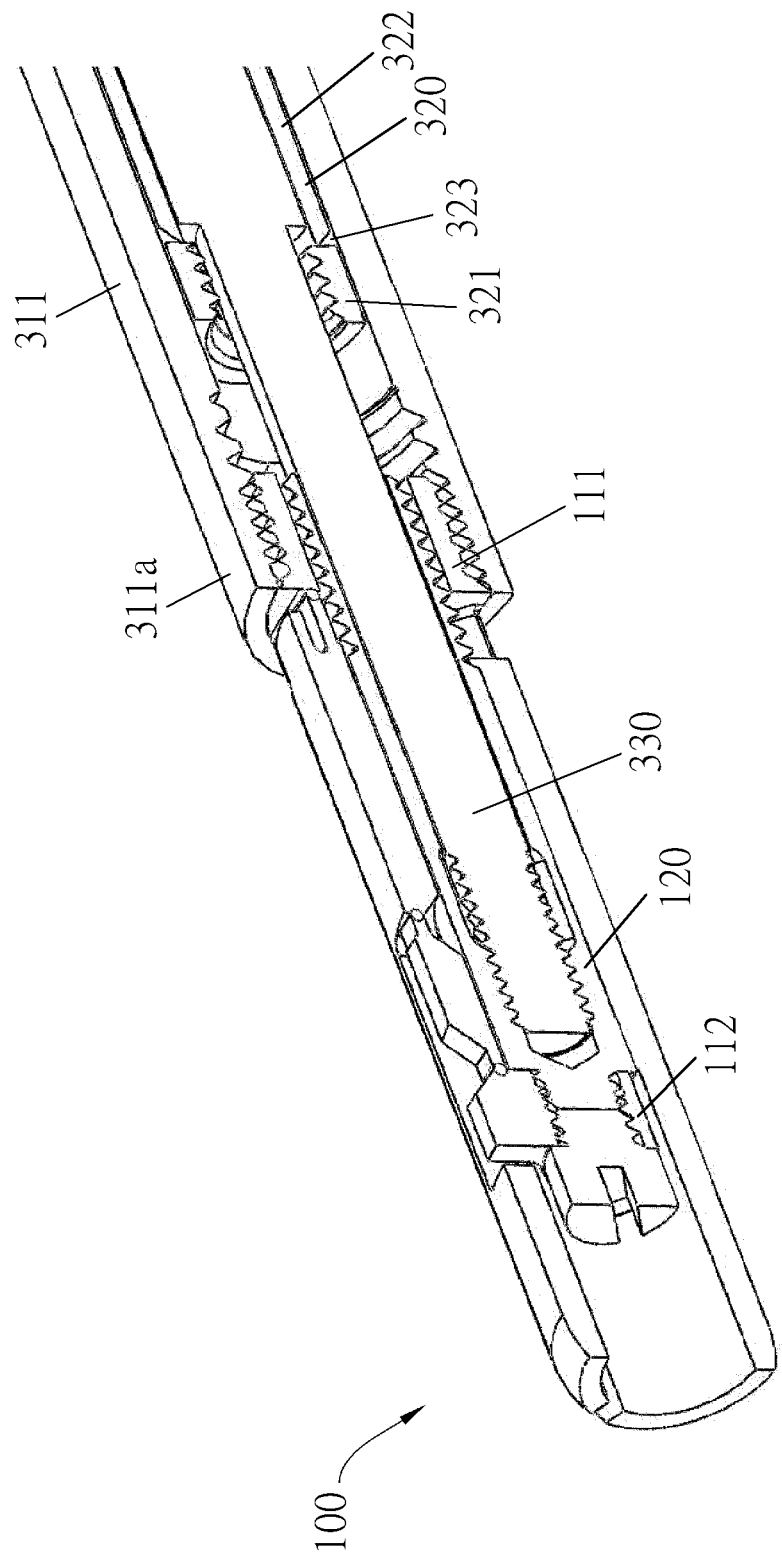
Figure 17A:
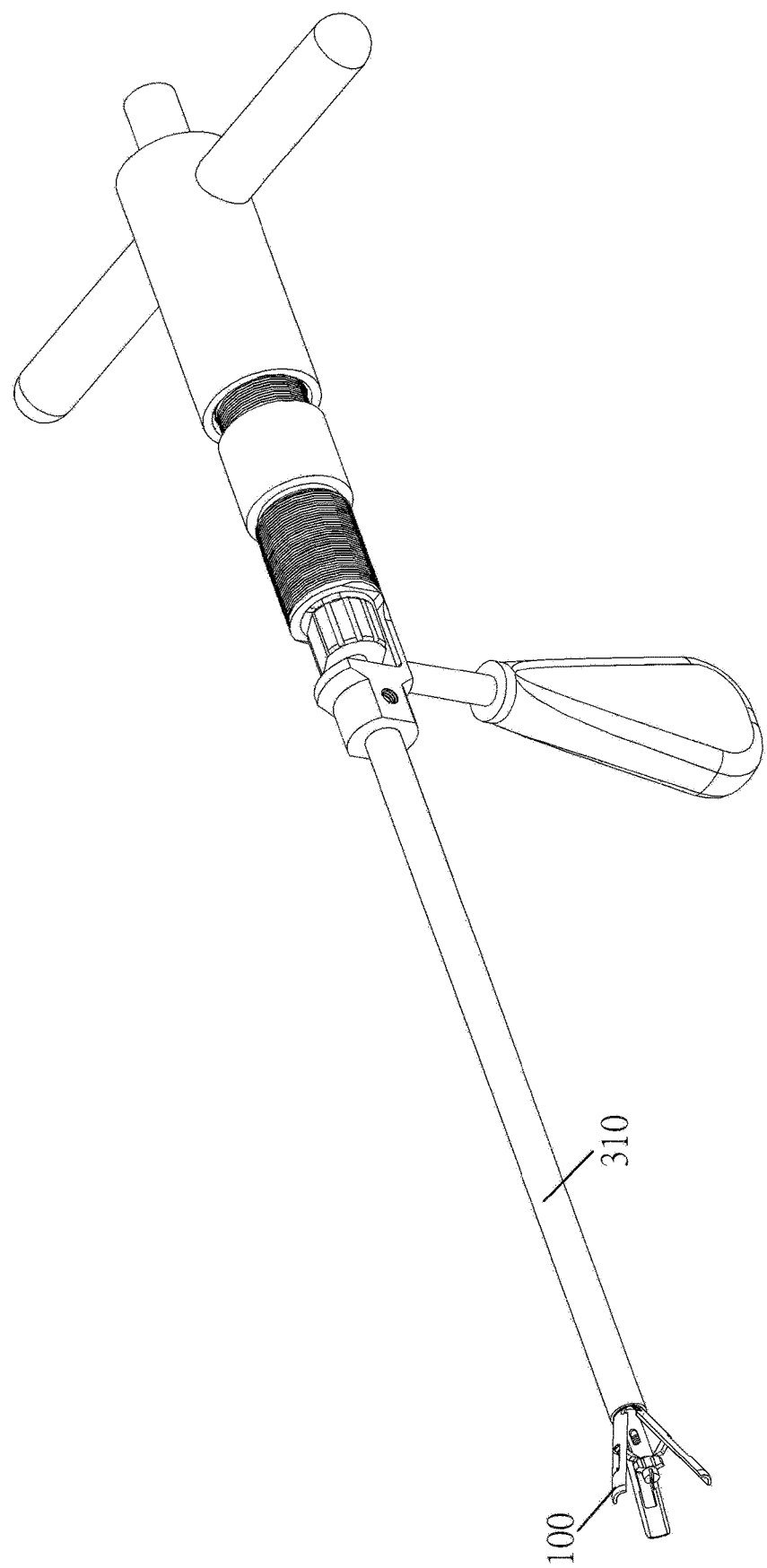
Figure 17B:
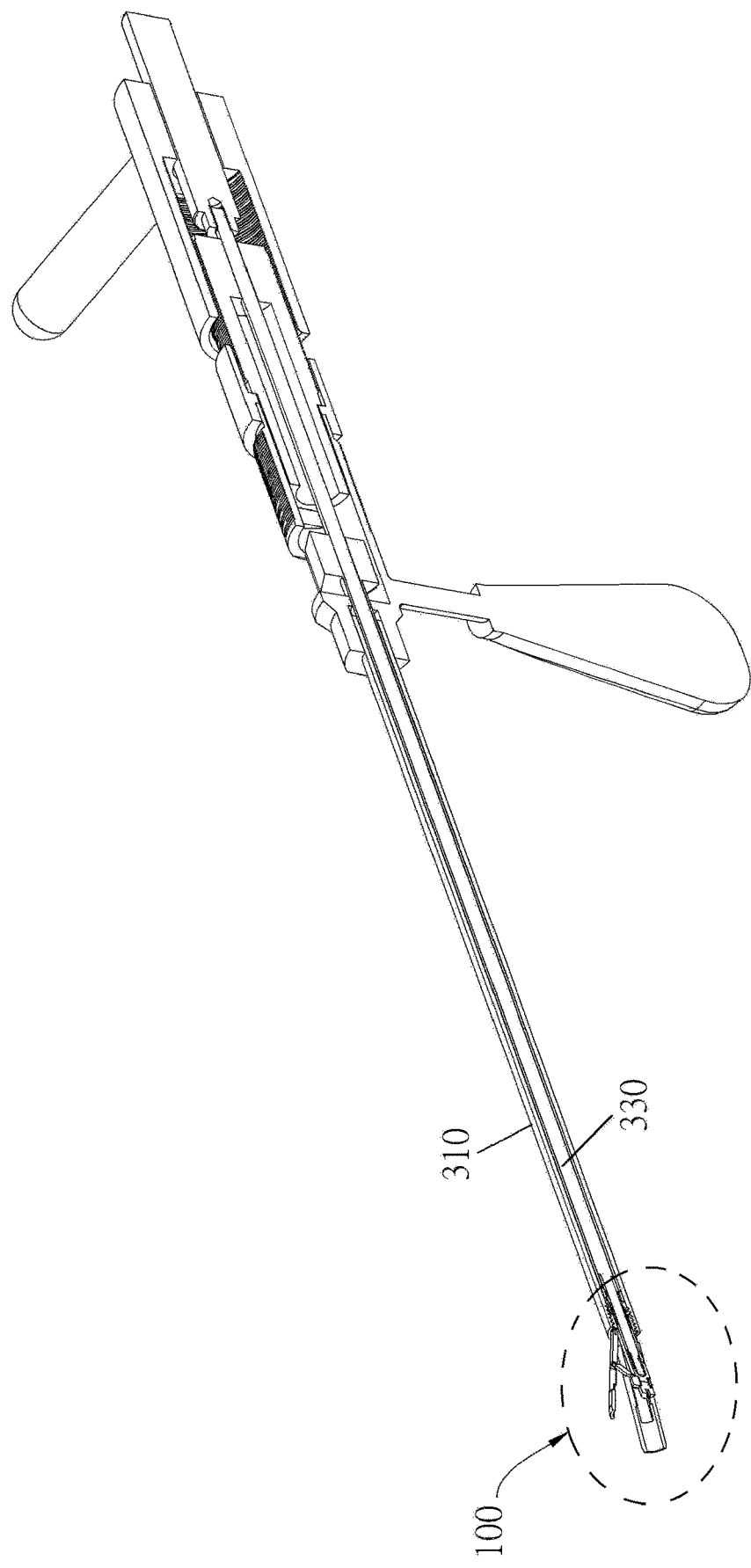
Figure 17C:
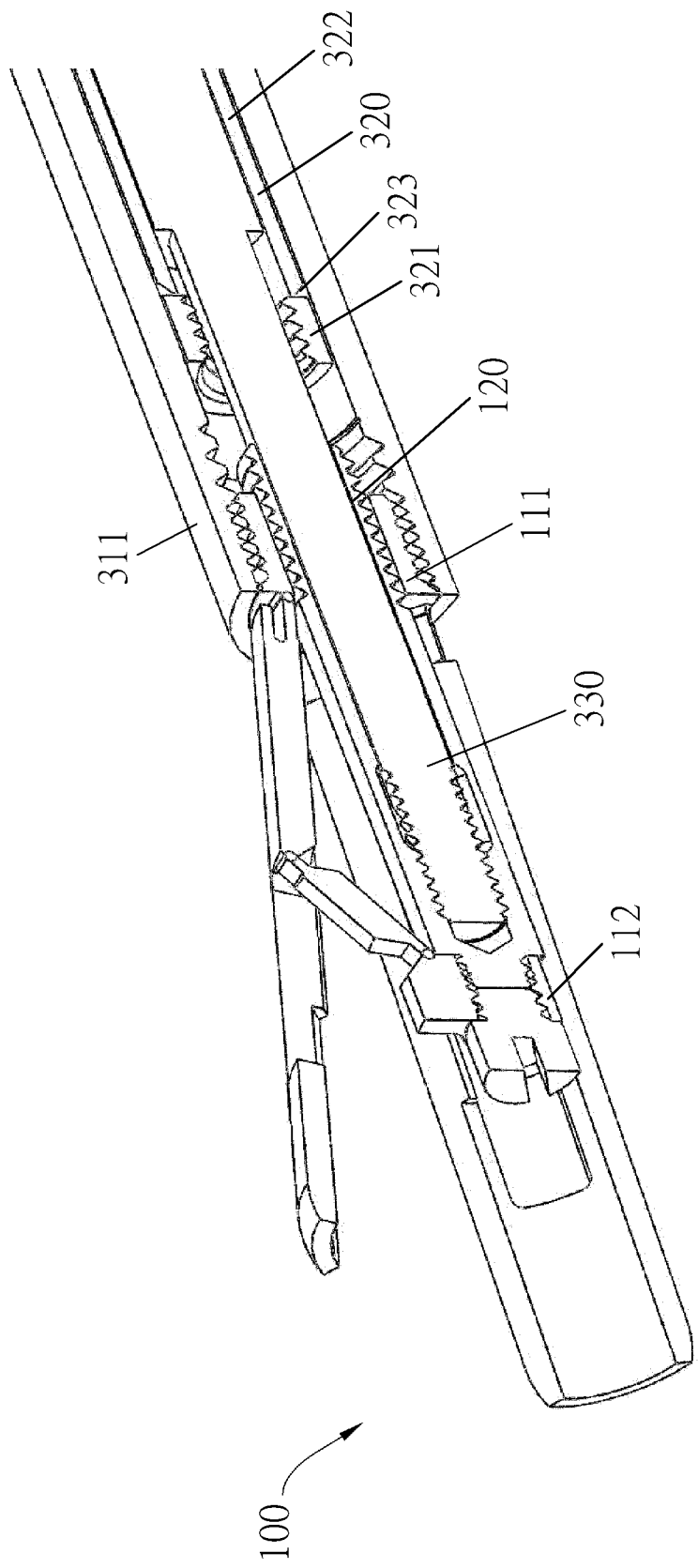
Figure 18A:
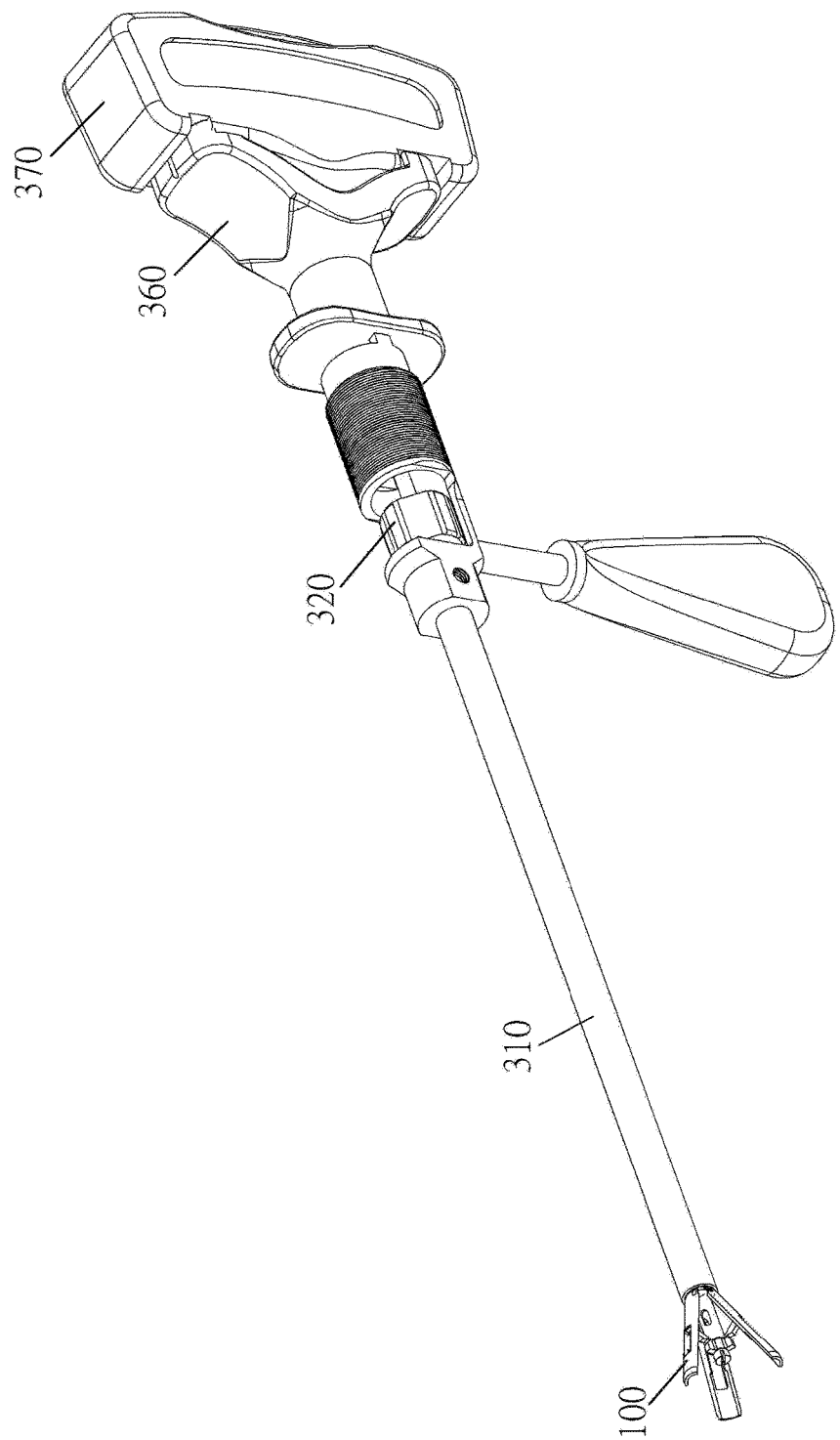
Figure 18B:
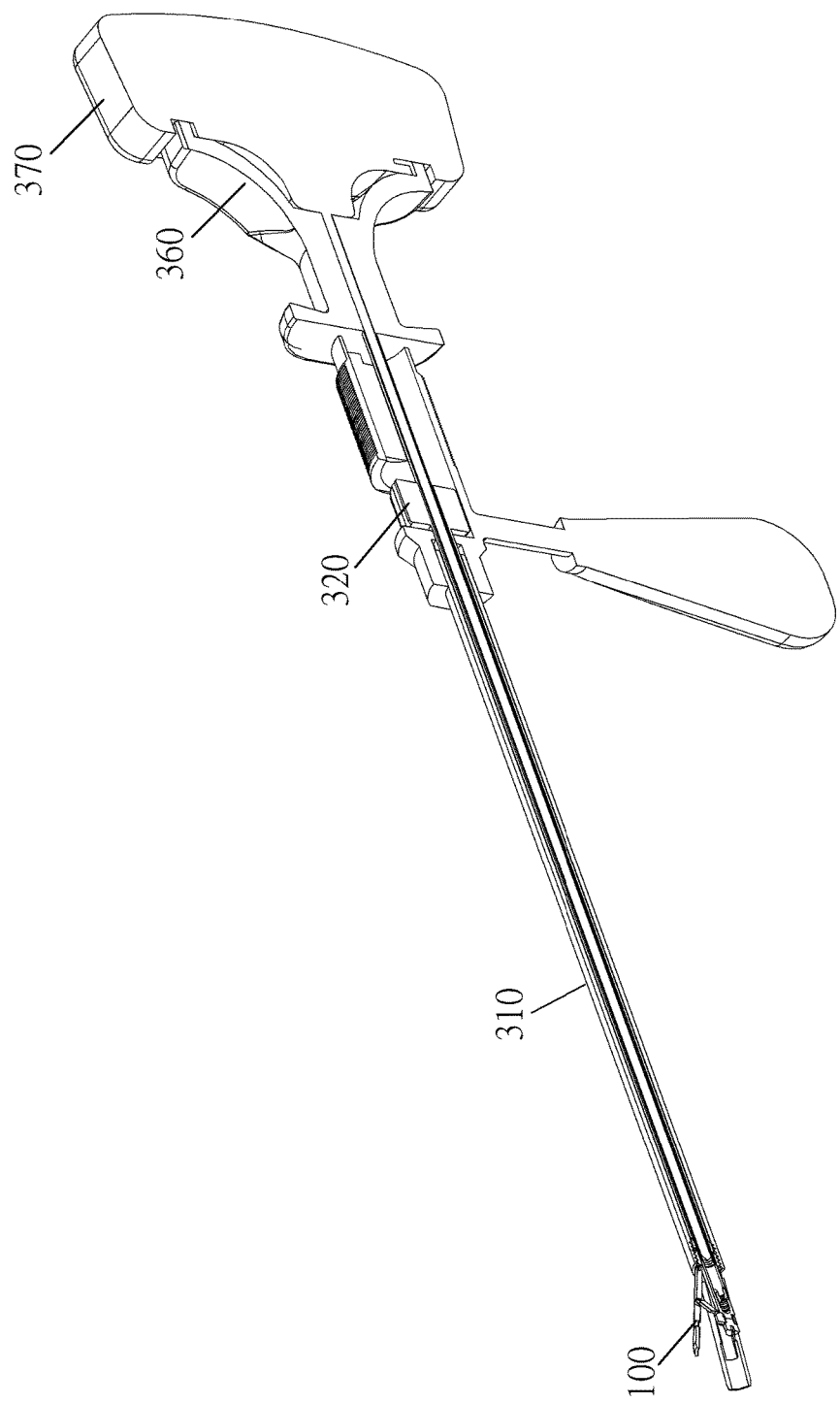

FIG. 16A through FIG. 17C are schematic views of the operating tool and the spinal implant structure 100 coupled thereto. FIG. 16A through FIG. 16C are schematic views of the operating tool and the spinal implant structure 100 coupled thereto and folded. FIG. 17A through FIG. 17C are schematic views of the operating tool and the spinal implant structure 100 coupled thereto and expanded. FIG. 16C and FIG. 17C are partial enlarged views of the junction of the operating tool and the spinal implant structure.

Referring to FIG. 16C, the tail 311a of the connecting portion 311 of the tool body 310 is operated in a manner to be jointed to the first part 111 of the spinal implant structure 100. FIG. 16C is exemplified by thread jointing. The central rod 330 (FIG. 11A) is rotated and inserted into the fixing screw barrel 120. Then, the operating handle 340 and converter 350 (FIG. 17A, 17B) are rotated, so as for the central rod 330 to be pulled backward, thereby effectuating the expansion of the spinal implant structure 100. Referring to FIG. 17C, upon completion of the expansion of the spinal implant structure 100, the fixing screw barrel 120 is at a location conducive to its operating the connecting portion 311 of the tool body 310; at this point in time, the user can move the fixing screw nut sleeve 320 (FIGS. 10A, 10B) of the operating tool leftward so that it fits around the fixing screw barrel 120 and thus gets fixed thereto. After the fixing screw nut sleeve 320 has fitted around the fixing screw barrel 120, the user rotates it again in the same direction and applies a torque thereto, so as to separate the fixing screw nut 321 and the sleeve 322 and finish the fixation process.

Figure 19A:
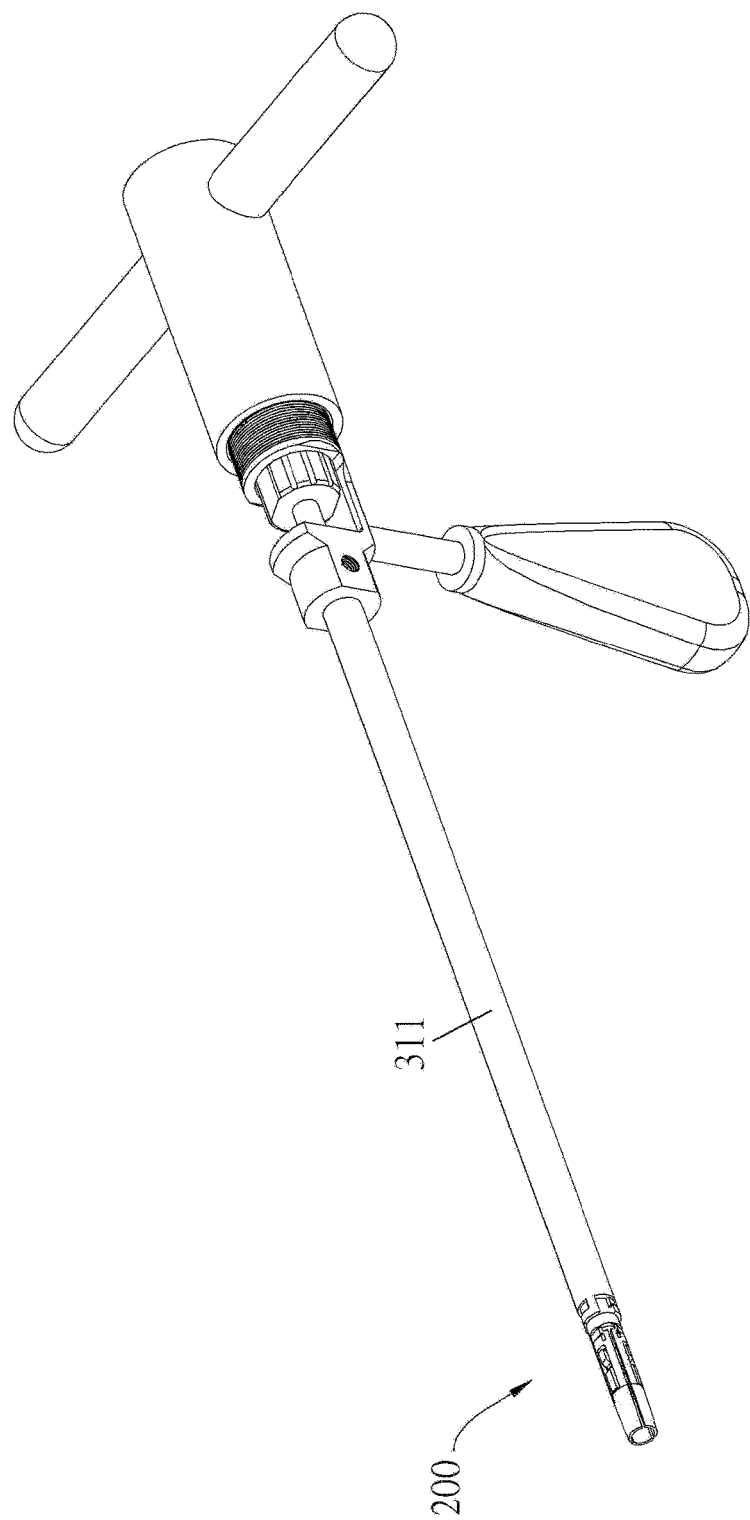
Figure 19B:
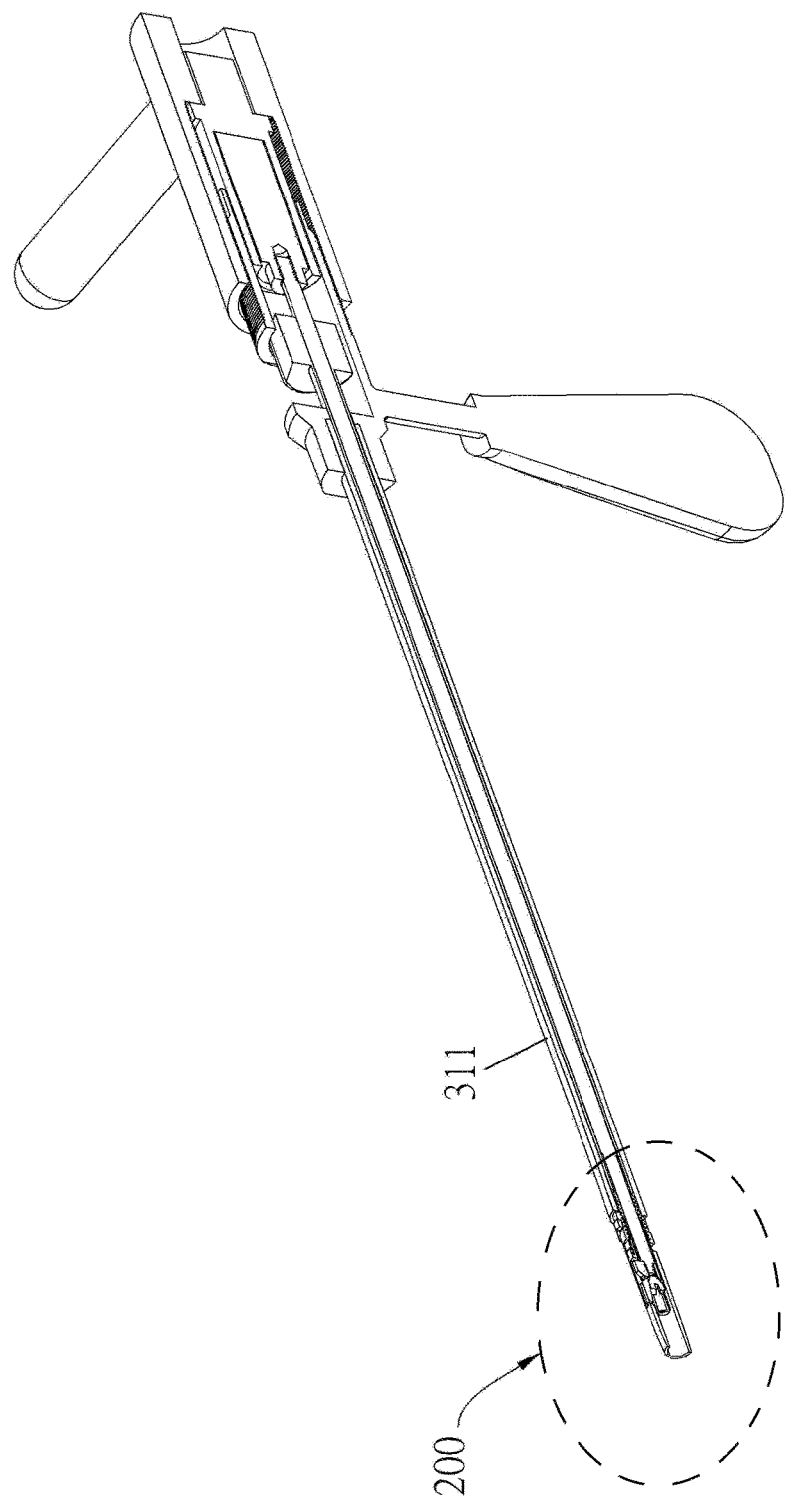
Figure 19C:
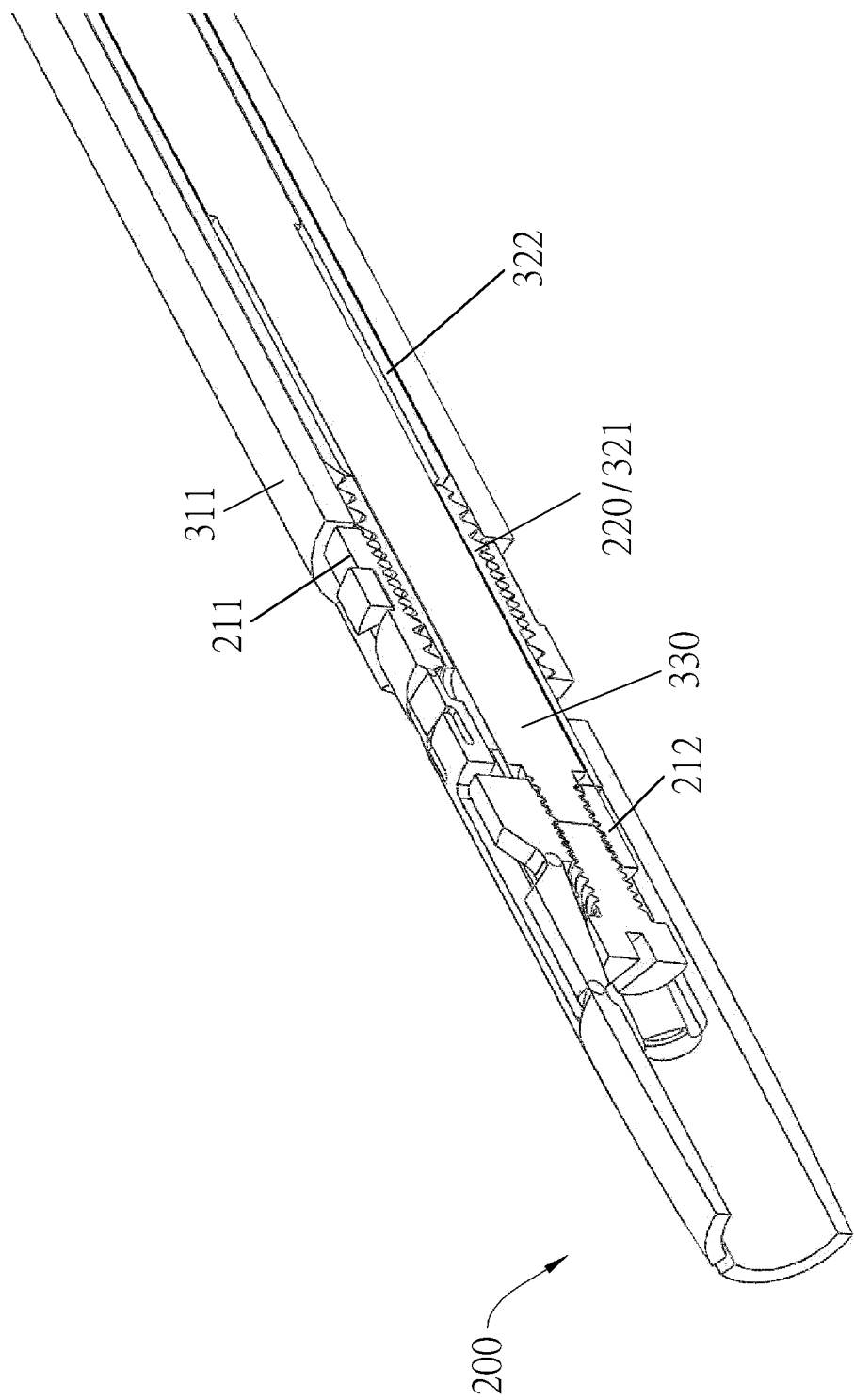
Figure 20A:
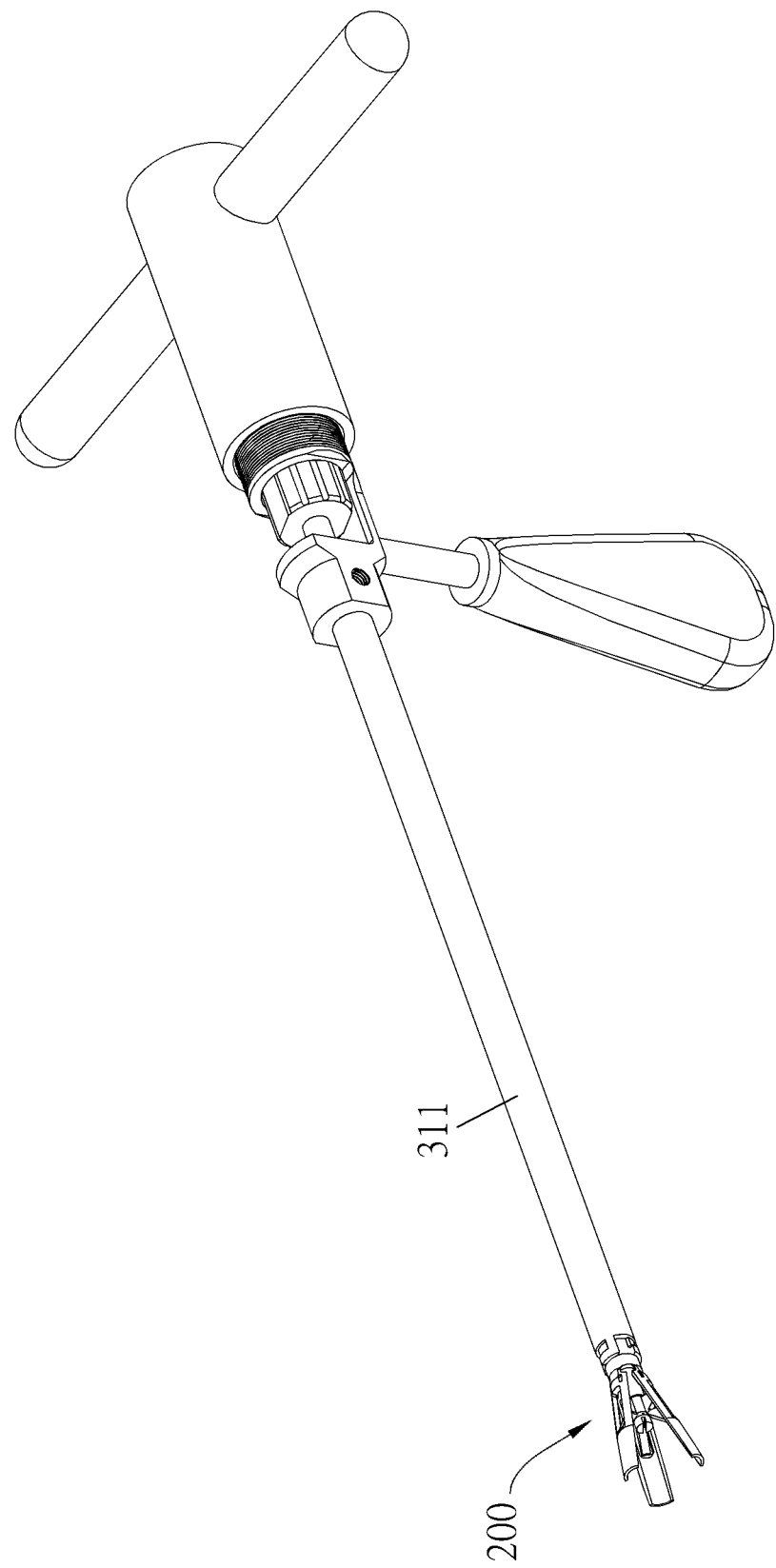
Figure 20C:
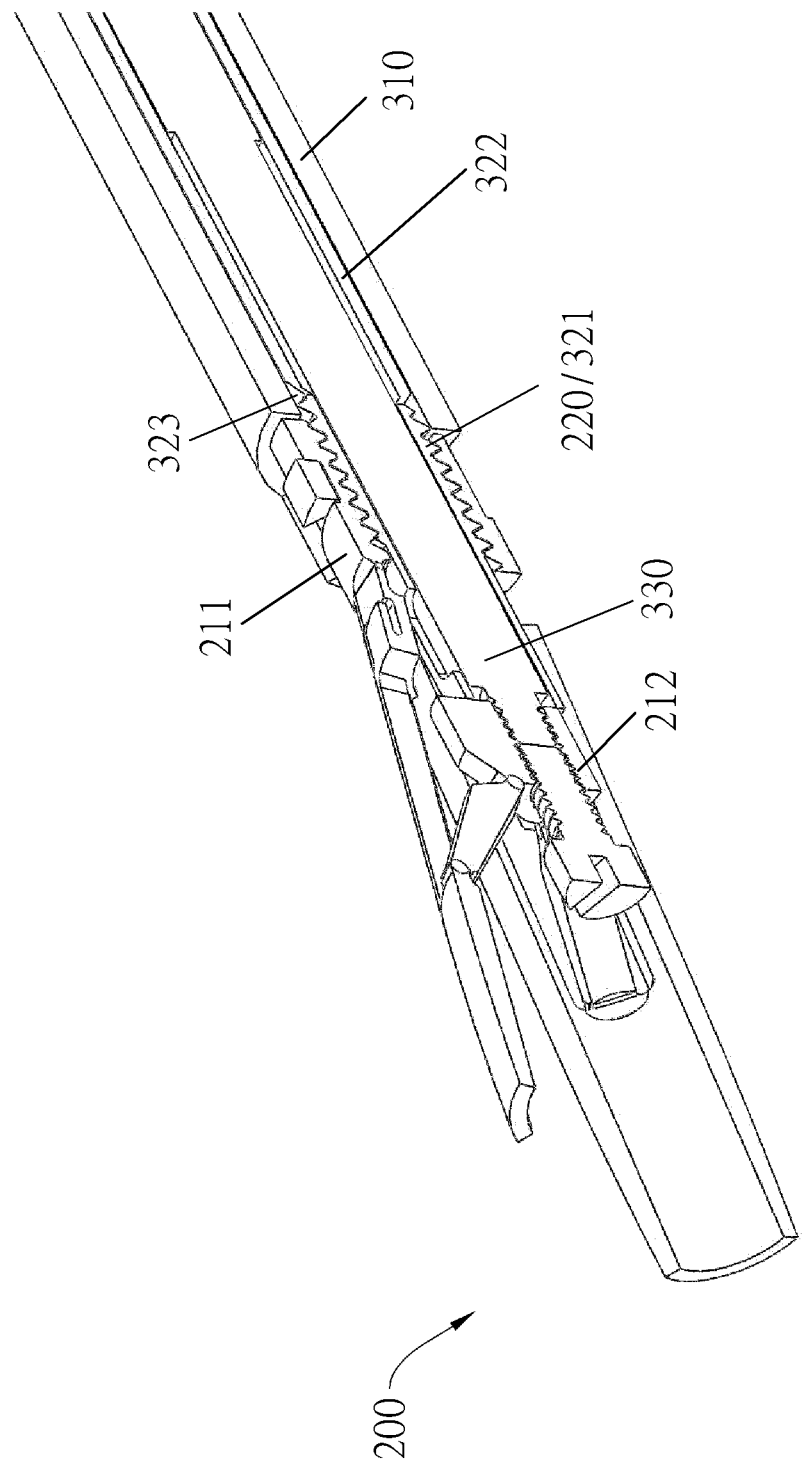

FIG. 19A through FIG. 20C are schematic views of the operating tool and the spinal implant structure 200 coupled thereto. FIG. 19A through FIG. 19C are schematic views of the operating tool and the spinal implant structure 200 coupled thereto and folded. FIG. 20A through FIG. 20C are schematic views of the operating tool and the spinal implant structure 200 coupled thereto and expanded. FIG. 19C and FIG. 20C are partial enlarged views of the junction of the operating tool and the spinal implant structure.

Referring to FIG. 19C, the tail 311a of the connecting portion 311 of the tool body 310 is jointed to the first part 211 of the spinal implant structure 200 by engagement for exemplary sake. The central rod 330 (FIG. 11B) is rotated and inserted into the second part 212. Then, the operating handle 340 and converter 350 (FIGS. 19A, 19B) are rotated so as to push the central rod 330 forward, thereby effectuating the expansion of the spinal implant structure 200. After the second part 212 has been pushed forward and fixed in place to effectuate the expansion of the spinal implant structure 200, as shown in FIG. 20C, the fixing screw barrel sleeve 320 (FIG. 10C) rotates and moves forward so that the front end of the fixing screw barrel sleeve 320 abuttingly connects with the second part 212 to fix it in place. At this point in time, the user rotates the fixing screw barrel sleeve 320 again in the same direction and applies a torque thereto, so as to separate the fixing screw barrel 321 and the sleeve 322, keep the fixing screw barrel 321, finish the fixation process, and remove the sleeve 322.

Due to the design of the expansion arm and the support arm of the spinal implant structure of the present invention, the spinal implant structure is steadily expanded within the vertebral body. Furthermore, the design of the netting of the spinal implant structure restricts the range of the flow of the bone cement, reduces the likelihood of a failure of vertebroplasty, and reinforces the vertebral body as a result of the expansion of the spinal implant structure.

Due to the design of the connection of the operating tool and the spinal implant structure of the present invention, not only are the spinal implant structure and the operating tool coupled together, but the expansion step and the bone cement perfusion step are also stable, thereby increasing the likelihood of successful vertebroplasty and reducing complications.

Although the operating tool of the present invention comprises many components, the components are not only easily put together and separated but also embody plenty practical operation-related advantages. When necessary, the user can easily disassemble the operating tool of the present invention and start to operate the spinal implant structure by hand so as to preclude any possible emergency. Therefore, the operating tool and the spinal implant structure of the present invention have advantages neither anticipated of nor achieved by conventional tools for use in vertebroplasty.

Although the present invention is disclosed above by embodiments, the embodiments are not restrictive of the present invention. Equivalent implementation of, or equivalent changes made to, the embodiments by persons skilled in the art without departing from the spirit of the present invention must be deemed falling within the scope of the present invention. Accordingly, the legal protection for the present invention should be defined by the appended claims.

What is claimed is:

1. A spinal implant structure, comprising:
   a first tube;
   a second tube disposed along a horizontal direction of the first tube without overlapping the first tube, the first tube having a larger diameter than that of the second tube; and
   at least one expansion arm with an end fixedly connecting with the first tube to form an included angle therebetween and another end being a free end, the at least one expansion arm having a support arm, the support arm having an end connecting with the expansion arm and another end fixedly connecting with the second tube,
   wherein the support arm, in response to a change in a distance between the first tube and the second tube, drives the expansion arm to move, thereby increasing the included angle and expanding the spinal implant structure.

2. The spinal implant structure of claim 1, wherein the at least one expansion arm is at least three expansion arms, and the expansion arms connected to the first tube are equally spaced apart.

3. The spinal implant structure of claim 1, wherein the included angle between the expansion arm and the first tube increases as the distance between the first tube and the second tube increases.

4. The spinal implant structure of claim 1, wherein the included angle between the expansion arm and the first tube decreases as the distance between the first tube and the second tube decreases.

5. The spinal implant structure of claim 1, further comprising:
   a fixing screw barrel fitting inside the first tube and having an end abuttingly connecting with the second tube to fix the distance between the first tube and the second tube.

6. The spinal implant structure of claim 5, wherein a wall of the fixing screw barrel has at least one through hole for perfusing a bone cement.

7. The spinal implant structure of claim 1, further comprising:
   a netting, wherein an end of the netting has at least one engaging hole whereby the end of the netting is engaged with the at least one expansion arm, and another end of the netting is fixed to the second tube through a fixing component so that the netting fits around an outer surface of the at least one expansion arm, wherein the fixing component is inserted into the second tube and has a head located outside the second tube, the netting is fixed in place at a junction of the head of the fixing component and the second tube to allow the netting to be unfolded as a result of the expansion of the spinal implant structure.

8. The spinal implant structure of claim 7, wherein the netting separates from the fixing component as a result of the expansion of the spinal implant structure.

9. The spinal implant structure of claim 1, wherein the first tube has an inner diameter larger than that of the second tube.

10. The spinal implant structure of claim 1, wherein the spinal implant structure has a larger volume in an expansion position than in a folded position.

11. A spinal implant kit, comprising:
the spinal implant structure of claim 1; and
an operating tool, comprising:
   a tool body comprising a connecting portion and a gripping portion, the connecting portion having a tail provided with a jointing structure having a thread structure for connecting with the spinal implant structure;
   a fixing sleeve fitting inside the tool body to fix a distance between the first tube and the second tube of the spinal implant structure;
   a central rod fitting inside the fixing sleeve to connect with the second tube directly or connect with the second tube through the fixing sleeve; and
   an operating handle connecting with the central rod and rotating to drive the central rod to move in a lengthwise direction of the first tube.

12. The spinal implant kit of claim 11, further comprising:
a bone cement perfusing sleeve fitting inside the fixing sleeve and the spinal implant structure to provide a path for perfusing a bone cement into the spinal implant structure; and
a bone cement ejector fitting inside the bone cement perfusing sleeve to push the bone cement into the spinal implant structure.

13. A spinal implant structure, comprising:
a first tube;
a second tube disposed along a horizontal direction of the first tube without overlapping the first tube, the first tube having a larger diameter than that of the second tube; and
at least one expansion arm with an end fixedly connecting with the first tube to form an included angle therebetween and another end being a free end, the at least one expansion arm having a support arm, the support arm having an end connecting with the expansion arm and another end fixedly connecting with the second tube,
wherein the support arm comprises a plurality of weakened sections so that, in response to a change in a distance between the first tube and the second tube, the support arm bends at the weakened sections and thus drives the expansion arm to move, thereby increasing the included angle and expanding the spinal implant structure.

* * * * *